(12) United States Patent
Josephson et al.

(10) Patent No.: US 7,829,350 B2
(45) Date of Patent: Nov. 9, 2010

(54) MAGNETIC-NANOPARTICLE CONJUGATES AND METHODS OF USE

(75) Inventors: Lee Josephson, Reading, MA (US); Ralph Weissleder, Peabody, MA (US); J. Manuel Perez, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 336 days.

(21) Appl. No.: 12/194,475

(22) Filed: Aug. 19, 2008

(65) Prior Publication Data
US 2009/0029392 A1    Jan. 29, 2009

Related U.S. Application Data

(63) Continuation of application No. 10/165,258, filed on Jun. 6, 2002, now abandoned.

(60) Provisional application No. 60/296,378, filed on Jun. 6, 2001.

(51) Int. Cl.
*G01N 33/00* (2006.01)
*G01N 33/48* (2006.01)
*G01N 33/50* (2006.01)
*G01N 33/543* (2006.01)
*G01N 33/553* (2006.01)
*G01N 33/86* (2006.01)
*B01L 3/00* (2006.01)

(52) U.S. Cl. .................. 436/526; 422/57; 422/68.1; 422/104; 435/6; 435/7.1; 435/7.5; 435/969; 436/518; 436/525; 436/528; 436/529; 436/548; 436/69; 436/73; 436/149; 977/773; 977/918; 977/920

(58) Field of Classification Search ............ None
See application file for complete search history.

(56) References Cited

U.S. PATENT DOCUMENTS

| 4,672,040 | A | 6/1987 | Josephson |
| 5,136,095 | A | 8/1992 | Tarnowski et al. |
| 5,164,297 | A | 11/1992 | Josephson et al. |

(Continued)

FOREIGN PATENT DOCUMENTS

WO    WO 90/06045    6/1990

(Continued)

OTHER PUBLICATIONS

Fry et al., "A new Approach to Template Purification for Sequencing Applications Using Paramagnetic Particles," *Research Report*, 13(1) (1992), pp. 124-131.

(Continued)

*Primary Examiner*—Unsu Jung
(74) *Attorney, Agent, or Firm*—Fish & Richardson P.C.

(57) ABSTRACT

The present invention provides novel compositions of binding moiety-nanoparticle conjugates, aggregates of these conjugates, and novel methods of using these conjugates, and aggregates. The nanoparticles in these conjugates can be magnetic metal oxides, either monodisperse or polydisperse. Binding moieties can be, e.g., oligonucleotides, polypeptides, or polysaccharides. Oligonucleotide sequences are linked to either non-polymer surface functionalized metal oxides or with functionalized polymers associated with the metal oxides. The novel compositions can be used in assays for detecting target molecules, such as nucleic acids and proteins, in vitro or as magnetic resonance (MR) contrast agents to detect target molecules in living organisms.

17 Claims, 10 Drawing Sheets

U.S. PATENT DOCUMENTS

| | | | |
|---|---|---|---|
| 5,254,460 | A | 10/1993 | Josephson et al. |
| 5,508,164 | A | 4/1996 | Kausch et al. |
| 5,512,439 | A | 4/1996 | Hornes et al. |
| 5,578,325 | A | 11/1996 | Domb et al. |
| 5,679,323 | A | 10/1997 | Menz et al. |
| 5,705,628 | A | 1/1998 | Hawkins |
| 5,801,003 | A | 9/1998 | Shimamura et al. |
| 5,898,071 | A | 4/1999 | Hawkins |
| 5,973,138 | A | 10/1999 | Collis |
| 6,007,845 | A | 12/1999 | Domb et al. |
| 6,361,944 | B1 | 3/2002 | Mirkin et al. |

FOREIGN PATENT DOCUMENTS

| | | |
|---|---|---|
| WO | WO 95/22963 | 8/1995 |
| WO | WO 96/09313 | 3/1996 |
| WO | WO 97/40181 | 10/1997 |
| WO | WO 98/04740 | 2/1998 |
| WO | WO 98/21587 | 5/1998 |
| WO | WO 01/00876 | 1/2001 |
| WO | WO 01/19405 | 3/2001 |

OTHER PUBLICATIONS

Högemann et al., "Improvement of MRI Probes to Allow Efficient Detection of Gene Expression," *Bioconjug. Chem.*, 11(6):941-946 (2000).

Josephson et al., "High-Efficiency Intracellular Magnetic Labeling with Novel Superparamagnetic-Tat Peptide Conjugates," *Bioconjug. Chem*, 10(2):186-191 (1999).

Josephson et al., "Magnetic Nanosensors for the Detection of Oligonucleotide Sequences," *Agnew. Chem. Int. Ed.*, 40(17):3204-3206 (2001).

Kötitz et al., "Determination of the Binding Reaction Between Avidin and Biotin by Relaxation Measurements of Magnetic Nanoparticles," *J. Magnetism and Magnetic Materials*, 194:62-68 (1999).

Lewin et al., "Tat Peptide-Derivatized Magnetic Nanoparticles Allow in vivo Tracking and Recovery of Progenitor Cells," *Nat. Bio.*, 18:410-414 (2000).

Niemeyer et al., "Self-Assembly of DNA-Streptavidin Nanostructures and Their Use as Reagents in Immuno-PCR," *Nucleic Acid Research*, 27(23):4553-4561 (1999).

Perez et al., "DNA-Based Magnetic Nanoparticle Assembly Acts as a Magnetic Relaxation Nanoswitch Allowing Screening of DNA-Cleaving Agents," *J. Am. Chem. Soc.*, 124(12):2856-2857 (2002).

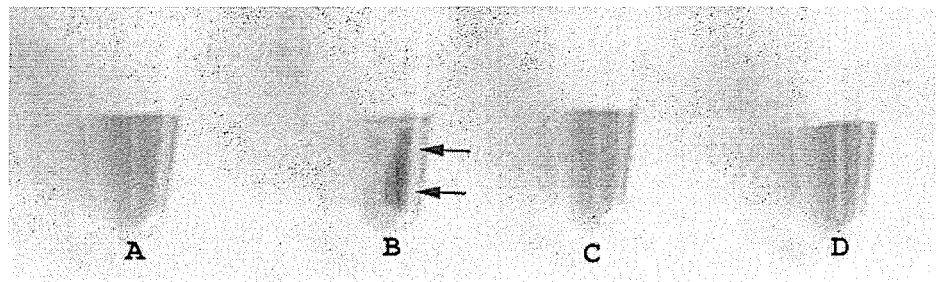
FIG. 2A     FIG. 2B     FIG. 2C     FIG. 2D
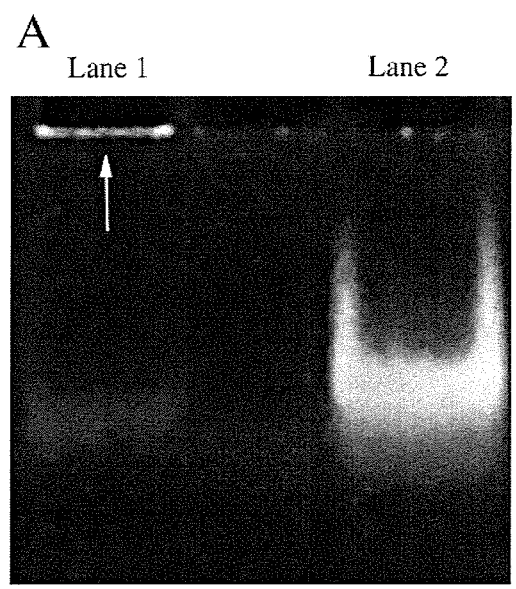 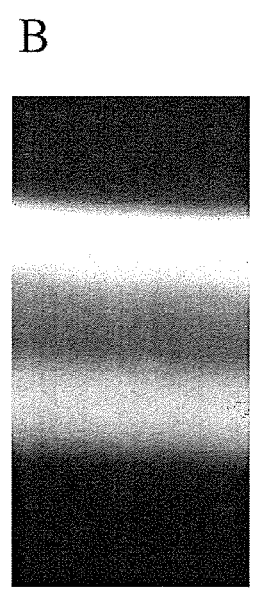
Complementary oligo
5',3' alkanethiooligo
FIG. 3A     FIG. 3B

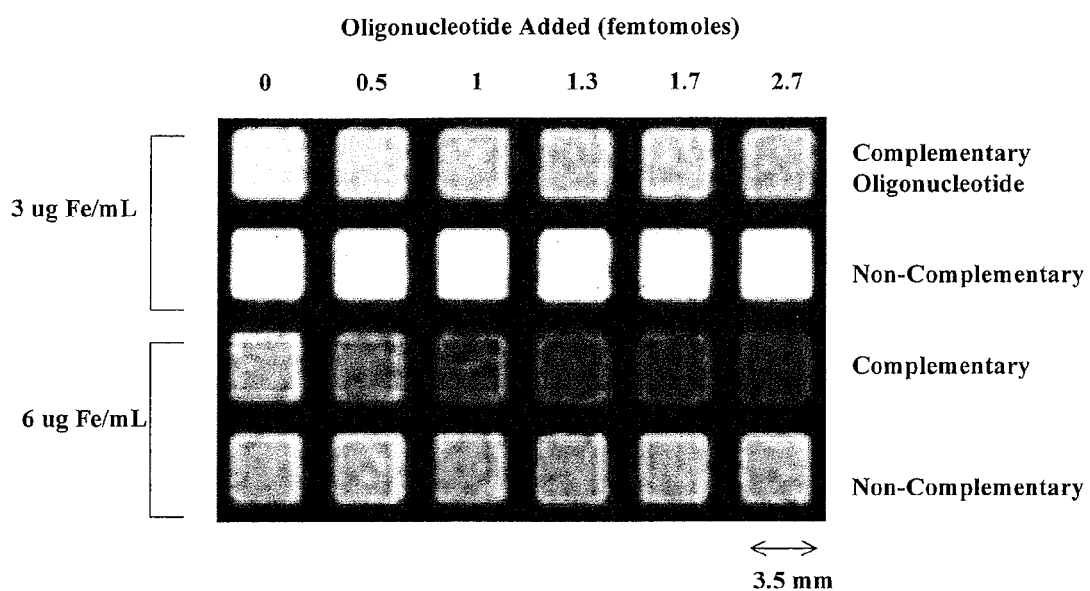
FIG. 7
G: TAA-ACG-GCC-ACA-AGT-TCG-GCG-TGT (SEQ ID NO:19)
A: TAA-ACG-GCC-ACA-AGT-TCA-GCG-TGT (SEQ ID NO:20)
T: TAA-ACG-GCC-ACA-AGT-TCT-GCG-TGT (SEQ ID NO:21)
C: TAA-ACG-GCC-ACA-AGT-TCC-GCG-TGT (SEQ ID NO:22)

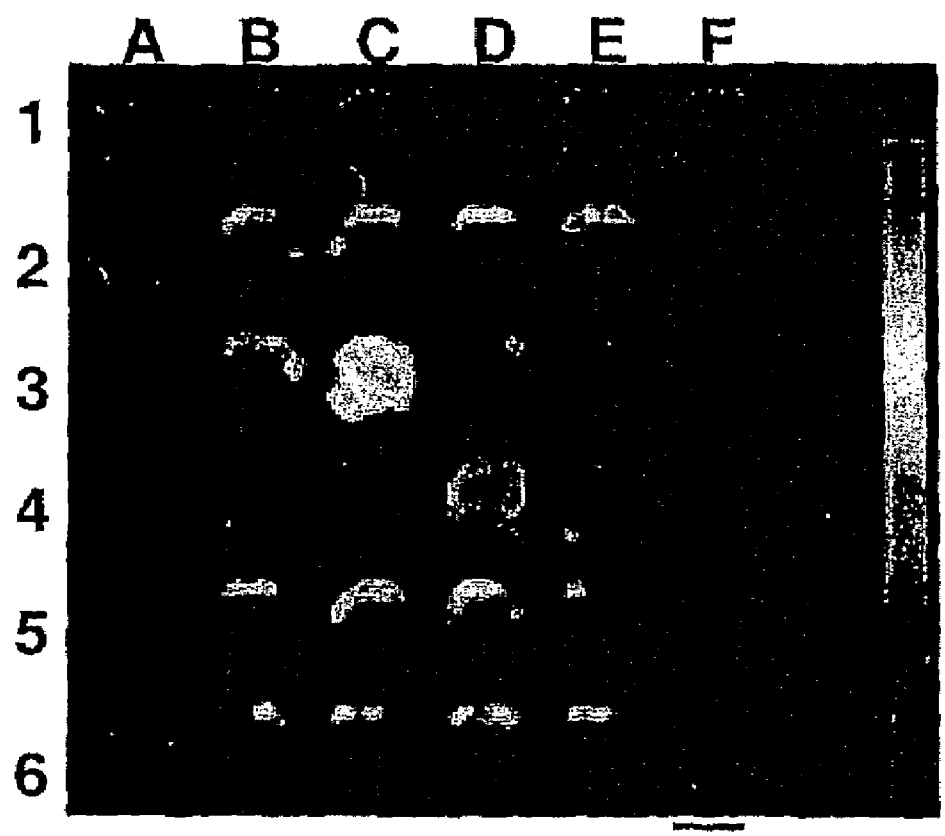
FIG. 9A  3.5 mm
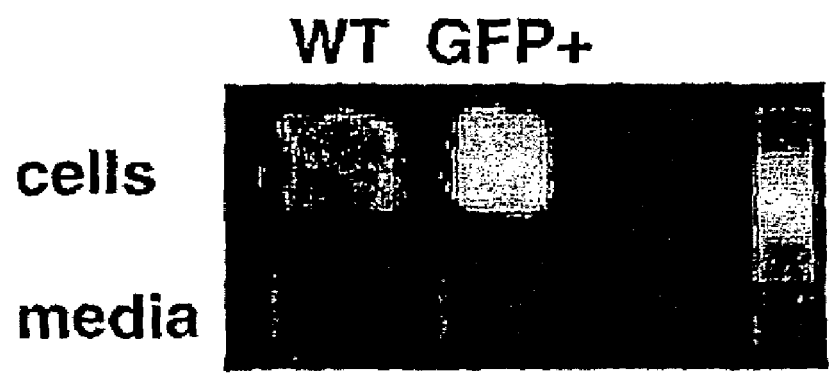
FIG. 9B  WT  GFP+

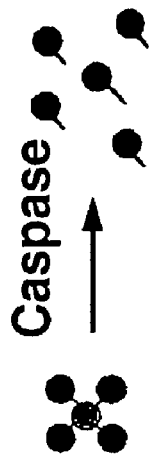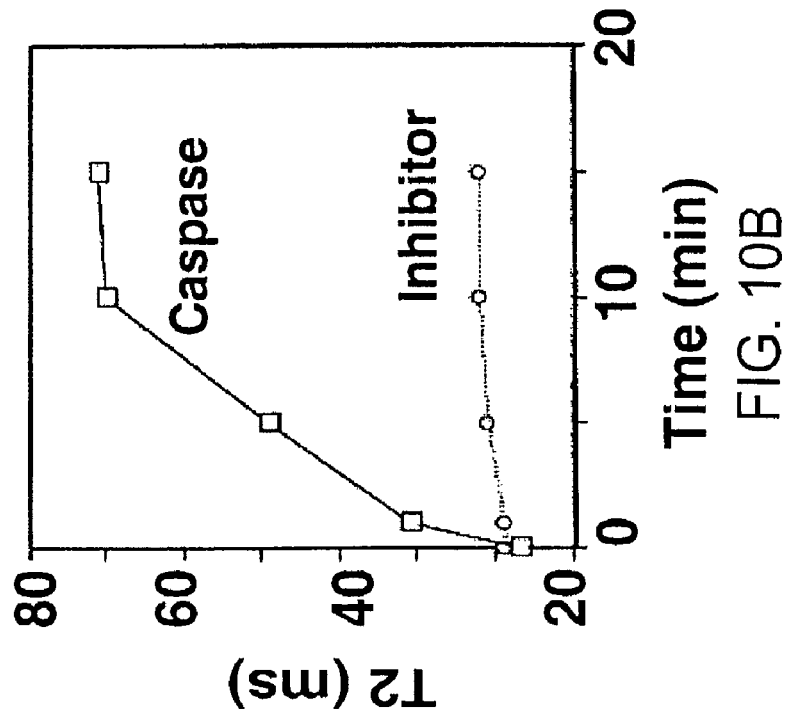
FIG. 10B
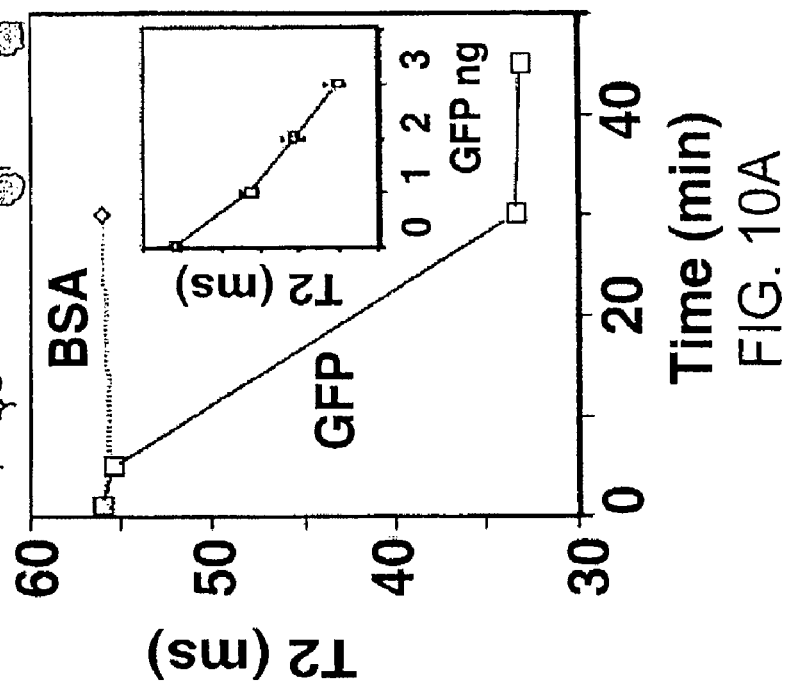
FIG. 10A

MAGNETIC-NANOPARTICLE CONJUGATES AND METHODS OF USE

CROSS-REFERENCE TO RELATED APPLICATION

This application is a continuation of U.S. patent application Ser. No. 10/165,258, filed on Jun. 6, 2002, which claims priority to U.S. Provisional Patent Application Ser. No. 60/296,378, filed on Jun. 6, 2001, both of which are incorporated herein by reference in their entirety.

TECHNICAL FIELD

This invention relates to magnetic nanoparticle conjugates and methods of use.

BACKGROUND

Magnetic particles are widely used reagents for the purification and extraction of nucleic acids. For example, U.S. Pat. Nos. 4,554,488 and 4,672,040 attach a nucleic acid to silanized magnetic particles that are about one micron in diameter. U.S. Pat. No. 5,898,071 utilizes one-micron silanized particles in the presence of polyethylene glycol (PEG) to extract DNA. Similar magnetic particles have been used to capture and release target nucleic acid for the detection of specific sequences of DNA (see, e.g., U.S. Pat. No. 5,750,338). Streptavidin has been attached to magnetic particles and can be used to recover biotinylated nucleic acids after sequence specific hybridization.

U.S. Pat. No. 5,512,439 describes attaching oligonucleotides to 1-10 micron microspheres impregnated with iron oxide and using the microspheres to bind to target nucleic acids, which can then be separated from their surrounding media.

U.S. Pat. No. 6,027,945 describes the use of magnetic silica particles having a diameter of 4-7 microns to extract and purify nucleic acids including DNA fragments, plasmid DNA, and RNA.

U.S. Pat. No. 5,508,164 describes linking chromosomes to silanized glass supports with disulfide crosslinking agents to link to cell organelles. Cell organelles are then labeled and biotinylated magnetic particles are used to magnetically recover the particles after separation from the solid support using reducing agents.

Preparations of magnetic particles designed for separation and extraction use particles that are amenable to easy manipulation by weak applied magnetic fields. These materials are typically micron sized and have a high magnetic moment per particle; their effects on water relaxation rate are unspecified and not relevant to their application. Nanoparticles do not respond to the weak, magnetic fields of hand held magnets.

Magnetic particles have also been used to assay for analytes based on their ability to bind analytes and change magnetic resonance (MR) relaxation rates. In U.S. Pat. No. 5,164,297, bovine serum albumin (BSA) coated magnetic particles were used to react with an antibody. Addition of BSA favors dissociation of the complex between the antibody and the BSA-coated iron oxide particles. As a result of this dissociation of aggregates, the solvent T2 relaxation time decreased (1/T2 increased) and the BSA concentration can be determined from T2.

In another example, WO 01/19405 describes the preparation and uses of magnetic nanoparticles with various biomacromolecules attached.

SUMMARY

The present invention provides new magnetic conjugates and methods for their synthesis and use. Each conjugate comprises a magnetic nanoparticle linked to a binding moiety that specifically binds to a target in a sample, such as a nucleic acid or protein, to another binding moiety on another conjugate, or to an aggregation inducing molecule, such as avidin. The novel compositions can be used in assays for detecting specific target molecules, such as biological molecules in sample solutions, e.g., by altering the magnetic resonance (MR) relaxation rate of the solution. Thus, the new conjugates can be considered to be magnetic relaxation switches (MRS).

The biological target molecules can be nucleic acid sequences (e.g., a sequence complementary to the binding moiety for hybridization), protein sequences (e.g., an antibody binding site), or polysaccharide sequences. Biological molecules are molecules of biological origin or synthetically made molecules that mimic the performance of biological molecules. Examples include, but are not limited to, peptides with non-natural amino acids, peptide nucleic acids (PNA's), or natural or man-made organic molecules that react with specific sites on target biological molecules.

The assay method is accomplished by synthesizing a population and, in some aspects of the invention, at least two populations of the binding moiety-nanoparticle conjugates. Each conjugate in a population has a plurality, e.g., two, three, four, or more, of a single type of binding moiety attached to a nanoparticle. The nanoparticle is composed of a magnetic metal oxide and one or more functional groups, e.g., a polymer comprising one or more functional groups. When polymers are included, they contain functional groups that enable the binding moiety to be attached to the nanoparticle to form the conjugate. The polymer can be a natural polymer, a synthetic polymer, a combination of natural and synthetic polymers, or derivatives of each type. The functional groups can be carboxy, amino, or sulfhydryl groups. In some embodiments, the binding moiety is attached to the nanoparticle through disulfide groups. The metal oxides can also be associated with non-polymer functional groups to form the nanoparticles.

In one aspect of the invention, a population of conjugates (or a mixture of two or more populations of conjugates with differing binding moieties directed to the same target molecule or type of target molecule) is placed into a sample solution. If the sample solution contains a target molecule to which the binding moieties specifically bind, the binding moieties interact with and bind to the target resulting in the formation (self-assembly) of aggregates, which are groups of 2 to about 20 conjugates bound together via a target molecule, an aggregation inducing molecule, or by their binding moieties. Thus, the dispersed state of the conjugates switches to an aggregate state, which decreases T2 relaxation times. FIG. 1 depicts one embodiment of such an interaction in which two conjugates, P1 and P2, combine to form an aggregate of six conjugates.

In another aspect of the invention, small aggregates of conjugates are prepared and then placed into a sample solution. In this assay system, the binding moieties when bound together to form the aggregates form a substrate that is cleaved by a specific target molecule, such as an enzyme that cleaves a specific site within a double-stranded nucleic acid formed by the hybridization of two single-strand oligonucleotide binding moieties. Alternatively, the binding moieties can be bound to an aggregation inducing molecule to form the aggregate. If the sample solution contains a target molecule, the substrate formed by the binding moieties is cleaved, resulting in the dissolution of the aggregates. Thus, the aggregate state switches to a dispersed state, which increases T2 relaxation times.

In various specific embodiments, the magnetic metal oxide contains superparamagnetic iron oxide crystals. The superparamagnetic character of the iron oxide of the nanoparticle makes it a potent enhancer of water relaxation rates, an enhancement that is altered when a target molecule binds specifically with a binding moiety of a conjugate to create an aggregate. Aggregates exert sensitive and reversible effects on the spin-spin relaxation of adjacent water protons upon hybridization in fluid phase. As a consequence, the presence of the target molecule interacting with the conjugate, in one embodiment, decreases T2.

The assays can be run in a single tube or in an array format, i.e., T2 can be determined for a single sample or for a number of samples simultaneously. The assays can be performed in fluid media that are optically transparent, optically translucent, optically opaque, or in turbid solutions. The fluid can be water, saline, buffered saline, or biological fluids, such as, but not limited to, blood, cell and/or tissue homogenates, extracts, suspensions, saliva, semen, milk, spinal fluid, and urine. Target molecules include sequences of nucleic acids unique to specific microorganisms such as viruses or bacteria or mRNA of specific genes expressed in specific cells (see below). The methods can also be used for genotyping DNA from humans or mammals.

In one embodiment, the invention features an aggregate including a plurality of conjugates, wherein each conjugate includes a magnetic nanoparticle linked to a binding moiety that specifically binds to a target molecule, to another binding moiety, or to an aggregation inducing molecule, and wherein each conjugate within the aggregate is bound to at least one other conjugate in the aggregate through their respective binding moieties. The aggregates can include 2 to about 20 conjugates, and can have a size of about 100 to 500 nm, e.g., 200, 300, or 400 nm.

The aggregates can also include a target molecule to which at least two different binding moieties specifically bind. In certain embodiments, the target molecule is a nucleic acid, and each binding moiety includes one of two or more different oligonucleotides, wherein each oligonucleotide is complementary to a region on the target nucleic acid that is different than the regions to which the other oligonucleotides are complementary. In other embodiments, the target molecule can be a polypeptide, and each binding moiety includes one of two or more different antibodies, wherein each antibody specifically binds to a binding site on the polypeptide that is different than the binding sites to which the other antibodies bind.

The aggregates can further include an aggregation inducing molecule, such as avidin or an antibody, wherein the binding moieties each selectively bind to the aggregation inducing molecule. For example, the binding moieties can include biotin.

In some embodiments, the binding moieties bind to each other to form the aggregate. For example, each binding moiety can include a cleavage site that is selectively cleaved by a target molecule, and cleavage of the binding moiety results in separation of the conjugates and dispersal of the aggregate. Alternatively, the binding moieties can be polypeptides and the target molecule can be an enzyme. In other examples, each binding moiety can bind to another binding moiety to form a cleavage site that is selectively cleaved by a target molecule, and cleavage of the binding moiety results in dispersal of the aggregate. For example, each binding moiety can include one of two complementary single-stranded oligonucleotides that hybridize to form a double-stranded nucleic acid comprising a cleavage site, and wherein the target molecule is an endonuclease.

"Linked" means attached or bound by covalent bonds, or non-covalent bonds, or other bonds, such as van der Waals forces.

"Specifically binds" means that one molecule, such as a binding moiety, e.g., an oligonucleotide or antibody, binds preferentially to another molecule, such as a target molecule, e.g., a nucleic acid or a protein, in the presence of other molecules in a sample.

In another aspect, the invention features a composition including a mixture of at least two populations of conjugates that specifically bind to a target molecule, wherein each conjugate in the first population comprises a nanoparticle including a magnetic metal oxide (e.g., a superparamagnetic metal oxide) linked to a plurality (e.g., two or three) of first binding moieties (e.g., oligonucleotides, polypeptides such as antibodies, and polysaccharides) that bind to a first binding site on the target molecule, and wherein each conjugate in the second population comprises a nanoparticle comprising a magnetic metal oxide linked to a plurality of second binding moieties that bind to a second binding site on the target molecule.

These compositions can include conjugates that further include functional groups that link the nanoparticles to the binding moieties. The functional groups can be amino, carboxy, or sulfhydryl groups. Alternatively, the conjugates can further include a polymer associated with the nanoparticles, and wherein the functional groups are bound to the polymer and to the binding moieties. The polymers can be hydrophilic, a natural or synthetic polymer, or a derivative of a natural or synthetic polymer. Examples of polymers include dextran, carboxymethyl dextran, reduced carboxymethyl dextran, crosslinked aminated dextran, pullanan, polyethylene glycol, and silane. In some embodiments, the binding moieties are attached to the functional groups through a covalent bond or by a disulfide bond. For example, oligonucleotides can be attached to the nanoparticles by a single covalent bond at the 3' or 5' end of each oligonucleotide.

In these compositions, the magnetic metal oxide can have a diameter between about 1 nm and about 25 nm, and the conjugate can have a diameter between about 15 nm and 100 nm, e.g., between about 40 nm and about 60 nm. In addition, each conjugate in the composition can have an R1 relaxivity between about 5 and 30 $mM^{-1} sec^{-1}$ and an R2 relaxivity between about 15 and 100 $mM^{-1} sec^{-1}$. In particular embodiments, the nanoparticle is an amino-derivatized cross-linked iron oxide nanoparticle.

In another aspect, the invention features a conjugate including a magnetic nanoparticle linked to a first binding moiety, wherein the first binding moiety includes a cleavage site for a target molecule and specifically binds to an aggregation inducing molecule, forms a cleavage site for the target molecule when the first binding moiety binds to a second binding moiety, or specifically binds to an aggregation inducing molecule that comprises a cleavage site. For example, the first binding moiety can include a polypeptide that has the cleavage site, and the target molecule can be an enzyme. Alternatively, the first binding moiety can bind to the second binding moiety to form the cleavage site that is selectively cleaved by a target molecule, wherein the target molecule is an enzyme. For example, the first and second binding moieties can be complementary single-stranded oligonucleotides that hybridize to form a double-stranded nucleic acid comprising the cleavage site, wherein the target molecule is an endonuclease.

In another example, the first binding moiety includes a polypeptide that contains the cleavage site and biotin, and the aggregation inducing molecule is avidin, or the first binding moiety includes avidin and the aggregation inducing molecule includes biotin and the cleavage site. The aggregation inducing molecule can also be an oligonucleotide with a biotin molecule at each end, wherein the cleavage site is an internal site, e.g., a site that is not at either end of the oligonucleotide. The aggregation inducing molecule can also include a polypeptide with a biotin molecule at each end, where the cleavage site is an internal site.

In another aspect, the invention features a method for determining the presence of a target molecule in a sample, by obtaining a mixture of at least two populations of conjugates that specifically bind to the target molecule to form an aggregate, wherein each conjugate in the first population includes a nanoparticle that includes a magnetic metal oxide linked to a plurality of first binding moieties that bind to a first binding site on the target molecule, and wherein each conjugate in the second population includes a nanoparticle including a magnetic metal oxide linked to a plurality of second binding moieties that bind to a second binding site on the target molecule; contacting the mixture with a fluid sample under conditions that enable the first and second binding moieties to specifically bind to any target molecules in the sample and form an aggregate of conjugates; and determining the presence of an aggregate in the sample, wherein the presence of the aggregate indicates the presence of the target molecule.

In this method, the presence of an aggregate can be determined by obtaining the relaxation properties of the fluid in the sample, wherein a change in the relaxation properties of the fluid indicates the presence of the target molecule. For example, a decrease in spin-spin relaxation time (T2) indicates the presence of the target molecule.

In certain embodiments, the target molecule is a nucleic acid, the first binding moieties are first oligonucleotides that are complementary to a first region of the target nucleic acid, and the second binding moieties are second oligonucleotides that are complementary to a second region of the target nucleic acid. In other embodiments, the target molecule is a polypeptide, the first binding moieties are first antibodies that specifically bind to a first binding site of the target polypeptide, and the second binding moieties are second antibodies that specifically bind to a second binding site of the target polypeptide. For example, the first and second antibodies can be monoclonal antibodies.

In another aspect, the invention features a method for determining the presence of a target molecule in a sample, by obtaining one or more populations of conjugates that are capable of forming an aggregate, wherein each conjugate in a first population includes a nanoparticle including a magnetic metal oxide linked to a first binding moiety, wherein the first binding moiety includes a cleavage site for the target molecule and specifically binds to an aggregation inducing molecule, forms a cleavage site for the target molecule when the first binding moiety binds to a second binding moiety in a second population of conjugates, or specifically binds to an aggregation inducing molecule that includes a cleavage site; mixing the conjugates of the one or more populations in a fluid under conditions that enable the binding moieties to specifically bind to each other or to an aggregation inducing molecule to form aggregates in the fluid; mixing the fluid containing the aggregates with a fluid sample under conditions that enable any target molecules in the sample to cleave the cleavage sites in the aggregates; and determining the presence of aggregates in the sample, wherein the absence of aggregates indicates the presence of the target molecule.

In this method, the absence of aggregates can be determined by obtaining the relaxation properties of the fluid in the sample, wherein a change in the relaxation properties of the fluid indicates the presence of the target molecule. For example, an increase in spin-spin relaxation time (T2) indicates the presence of the target molecule.

In this method, the target molecule can be an enzyme, and the first binding moiety can include a polypeptide that contains the cleavage site. In addition, the binding moieties can be a polypeptide that contains the cleavage site and biotin, and the aggregation inducing molecule can be avidin. In some embodiments, the target molecule is an endonuclease, and the first and second binding moieties are complementary single-stranded oligonucleotides that hybridize to form a double-stranded nucleic acid comprising the cleavage site selectively cleaved by the endonuclease. In other embodiments, the first binding moiety includes avidin and the aggregation inducing molecule includes biotin and the cleavage site. For example, the aggregation inducing molecule can include an oligonucleotide or polypeptide with a biotin molecule at each end, and the cleavage site is an internal site.

In another aspect, the invention features a method for determining the presence of a target molecule in a sample, by obtaining first and second populations of oligonucleotide-nanoparticle conjugates, wherein each conjugate in the first population includes a nanoparticle having a magnetic metal oxide associated with a polymer having functional groups; and a plurality of first oligonucleotides attached to the functional groups on the nanoparticle; and wherein each conjugate in the second population includes a nanoparticle having a metal oxide associated with a polymer having functional groups; and a plurality of second oligonucleotides attached to the functional groups on the nanoparticle; wherein the first and second oligonucleotides are each complementary to first and second portions of the target nucleic acid, and wherein the oligonucleotides in each population are the same on each conjugate in the population and different than the oligonucleotides on the conjugates in the other populations; preparing a mixture of the first and second populations of oligonucleotide-nanoparticle conjugates; obtaining a fluid sample; contacting the mixture with the sample under conditions that enable any target nucleic acid in the sample to hybridize to the first and second oligonucleotides of both populations of conjugates; and obtaining the relaxation properties of the fluid in the sample, wherein a change in the relaxation properties of the fluid indicates the presence of the target nucleic acid.

In other aspects, the invention includes assays for determining aggregate formation in a fluid sample by adding a new composition of the invention to the fluid sample under conditions that enable aggregate formation; and measuring the relaxation properties of the sample over time after addition of the composition, wherein a decrease in spin-spin relaxation (T2) indicates aggregate formation. In another version, the invention includes assays for determining aggregate dispersal in a fluid sample by adding an aggregate formed from the new conjugates to the fluid sample under conditions that enable cleavage of the aggregate; measuring the relaxation properties of the sample over time after addition of the conjugate, wherein an increase in spin-spin relaxation (T2) indicates aggregate dispersal.

In the new methods, the sample fluid can be optically transparent, optically translucent, optically turbid, or optically opaque. The fluid can be water, saline, buffered saline, or a biological fluid. The biological fluid can be blood, a cell homogenate, a tissue homogenate, a cell extract, a tissue extract, a cell suspension, a tissue suspension, milk, urine, saliva, semen, or spinal fluid.

In these methods, the amount of change in the relaxation properties can indicate a concentration of target molecules in the sample.

In another aspect, the invention features a method for purifying a target molecule (such as a nucleic acid or polypeptide) from a sample by obtaining a conjugate including a nanoparticle having a magnetic metal oxide linked by a cleavable bond (e.g., a reducible disulfide bond) to a binding moiety that specifically binds to a binding site on the target molecule; obtaining a sample containing the target molecule in a fluid; mixing the conjugates with the sample under conditions sufficient to enable target molecules in the sample to bind to the binding moiety on the conjugate to form target molecule-binding moiety complexes; separating the conjugates from the sample; and cleaving the cleavable bond to separate the target molecule-binding moiety complexes from the conjugates, thereby purifying the target molecules.

In the methods for the extraction and purification of nucleic acids or materials hybridizing to nucleic acids. The conjugates can be oligonucleotide-nanoparticle conjugates having a reducible disulfide bond to couple the oligonucleotides to the nanoparticles, and as a result reducing agents can separate the oligonucleotides from the nanoparticles at a desired time. Materials bound to the oligonucleotide portion of these oligonucleotide nanoparticle conjugates, such as double-stranded nucleic acids, can be obtained by the use of reducing agents rather than by use of the high ionic strength, chaotropic agents, or extremes of pH, that are required in previously known methods.

The invention also includes an assay for simultaneously determining the presence of a target nucleic acid in a plurality of samples, by obtaining first and second populations of oligonucleotide-nanoparticle conjugates, wherein each conjugate in the first population includes a nanoparticle having a magnetic metal oxide associated with a polymer having functional groups; and a plurality of first oligonucleotides attached to the functional groups on the nanoparticle, and wherein each conjugate in the second population includes a nanoparticle having a metal oxide associated with a polymer having functional groups; and a plurality of second oligonucleotides attached to the functional groups on the nanoparticle; wherein the first and second oligonucleotides are each complementary to first and second portions of the target nucleic acid, and wherein the oligonucleotides in each population are the same on each conjugate in the population and different than the oligonucleotides on the conjugates in the other populations; preparing a mixture of the first and second populations of oligonucleotide-nanoparticle conjugates; obtaining a plurality of fluid samples; contacting a portion of the mixture with each of the plurality of samples under conditions that enable any target nucleic acid in the samples to hybridize to the first and second oligonucleotides of both populations of oligonucleotide-nanoparticle conjugates; and simultaneously obtaining the relaxation properties of the fluid in each of the plurality of samples, wherein a change in the relaxation properties of a sample indicates the presence of the target nucleic acid in that sample.

In this method, the amount of change in the relaxation properties of a sample can indicate a concentration of target nucleic acid in that sample.

The invention also features a method for determining the presence of a target molecule in a subject by administering to the subject at least one population of conjugates, wherein each conjugate includes a nanoparticle having a magnetic metal oxide linked to a binding moiety that specifically binds to the target molecule; providing sufficient time for the binding moieties to bind to target molecules in the subject; and generating a magnetic resonance (MR) image of the subject, wherein a signal in the image indicates the presence of a target molecule. For example, the target molecule can be a nucleic acid or protein, and the binding moiety can be an oligonucleotide that is complementary or an antibody that specifically binds to a portion of the target nucleic acid. In one embodiment, at least two populations of conjugates are administered to the subject, wherein the binding moieties on the conjugates in each population are identical within the population and different from the binding moieties on the conjugates in other populations; and wherein the binding moieties in different populations of conjugates specifically bind to different portions of the target molecule.

In another aspect, the invention features a method for determining the levels of mRNA in cells using a mixture of populations of superparamagnetic oligonucleotide-iron oxide nanoparticle conjugates and MR imaging. When the conjugates react with a target, e.g., mRNA, the relaxation rate of the solvent changes. Hence, the level of an mRNA in a sample can be determined from measurements of spin-spin or spin-lattice relaxation times of water. In another embodiment, a detector is used that can simultaneously measure the relaxation properties of many spatially separated samples simultaneously, e.g., in an array format. In yet another embodiment, the invention features a method in which the oligonucleotide-nanoparticle conjugates and an MR detector are used to determine the pattern of gene expression in an organism.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 2A to 2D are images of test tubes illustrating the effect of incubating oligonucleotide-nanoparticle conjugates with oligonucleotides. From left to right, 2A: P1 and P2; 2B: P1, P2 plus complementary oligonucleotide; 2C: P1, P2 plus half-complementary oligonucleotide; 2D: P1, P2 and non-complementary oligonucleotide. The precipitate in the tube in FIG. 2B was moved to the side with a hand held magnet as indicated by two arrows.

FIGS. 3A and 3B are images of gel electrophoresis of a P1/P2/oligonucleotide nanoparticle precipitate. FIG. 3A shows a gel run in non-denaturing conditions. Lane 1: No DTT. Oligonucleotide remains with P1/P2 at the top of the gel (arrow). Lane 2: With DTT. A single band of double stranded oligonucleotide is seen. FIG. 3B shows a gel run with denaturing conditions and with DTT. Two bands are evident, the complementary oligonucleotide (slower band) and a band of 5' and 3' alkanethioligonucleotides (faster band).

FIG. 7 is an MR image showing the signal intensity of 24 wells of a 384 well microtiter plate. Wells had 3 or 6 Tg Fe/mL as mixture of P1 and P2. Wells had the indicated amounts of either complementary or noncomplementary oligonucleotide.

FIG. 9A is an image of a section of a 384 well plate containing GFP-P1 and GFP-P2 with total RNA extracted from various cell lines. FIG. 9B is an image of the nanoparticle conjugates with lysed cells from WT or GFP+human glioma lysate two hours following hybridization.

FIG. 10A is a graph illustrating the incubation of anti-GFP-P1 nanoparticle conjugates with GFP or BSA protein resulting in a significant decrease in T2. FIG. 10B is a graph illustrating the incubation of an aggregate of conjugates, each containing a DEVD peptide, with the enzyme caspase, which cleaves the DVED peptide sequence resulting in a dissolution of the conjugates, and an increase of T2 relaxation time.

DETAILED DESCRIPTION

Figure 1:
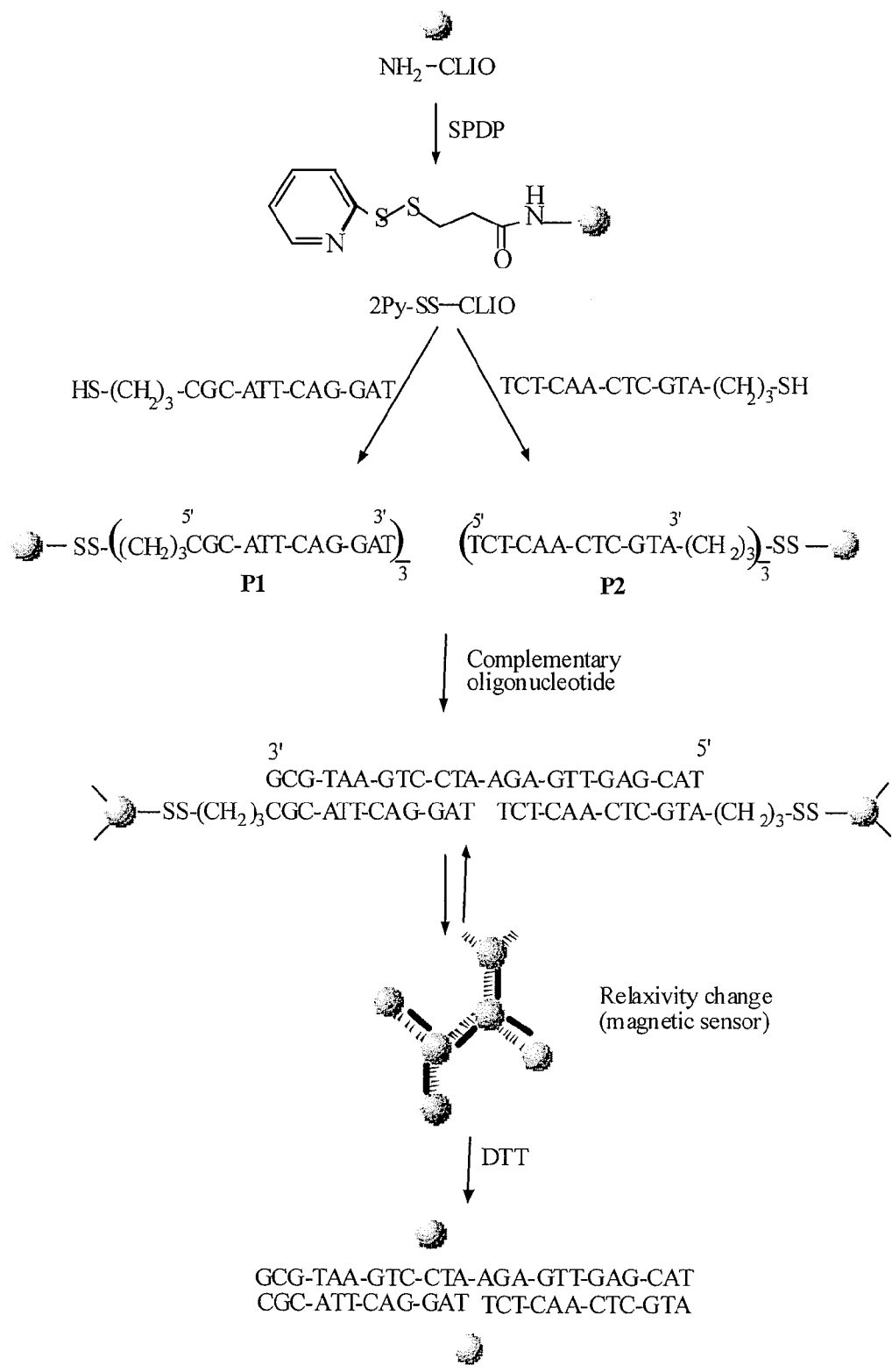
FIG. 1 is a schematic diagram showing a reaction scheme in which alkanethiooligonucleotides were reacted with N-succinimidyl 3-(2-pyridyldithio) propionate (SPDP) activated nanoparticles to form nanoparticle conjugates P1 and P2. P1 and P2 hybridize with complementary oligonucleotides followed by aggregation and magnetic relaxivity changes. Dithiothreitol (DTT) treatment breaks the bond between nanoparticle and alkanethiooligonucleotide.

The present invention provides compositions of conjugates and aggregates of conjugates, and methods of making and using these conjugates and aggregates. Each conjugate comprises one or more binding moieties (e.g., an oligonucleotide, nucleic acid, polypeptide, or polysaccharide) linked, e.g., covalently or non-covalently, to a magnetic, e.g., superparamagnetic, nanoparticle. The binding moiety causes a specific interaction with a target molecule (or, in some embodiments, an aggregation inducing molecule, such as avidin). Either, the binding moiety specifically binds to a selected target molecule, which can be, for example, a nucleic acid, polypeptide, or polysaccharide, or the binding moiety can be designed to bind to another binding moiety to form a substrate that is cleaved by the target molecule. Binding causes aggregation of the conjugates, resulting in a decrease of the spin-spin relaxation time (T2) of adjacent water protons in an aqueous solution. Cleavage causes dispersal of the aggregate into separate conjugates, resulting in an increase of the spin-spin relaxation time (T2) of adjacent water protons in an aqueous solution.

Nanoparticles

Nanoparticles can be monodisperse (a single crystal of a magnetic material, e.g., metal oxide, such as superparamagnetic iron oxide, per nanoparticle) or polydisperse (a plurality of crystals, e.g., 2, 3, or 4, per nanoparticle). The magnetic metal oxide can also comprise cobalt, magnesium, zinc, or mixtures of these metals with iron. The term "magnetic" as used in this specification and the accompanying claims means materials of high positive magnetic susceptibility such as superparamagnetic compounds and magnetite, gamma ferric oxide, or metallic iron. Important features and elements of nanoparticles that are useful to produce the new conjugates include: (i) a high relaxivity, i.e., strong effect on water relaxation, (ii) a functional group to which the binding moiety can be covalently attached, (iii) a low non-specific binding of interactive moieties to the nanoparticle, and (iv) stability in solution, i.e., the nanoparticles do not precipitate.

In all embodiments, the nanoparticles are attached (linked) to the binding moieties via functional groups. In some embodiments, the nanoparticles are associated with a polymer that includes the functional groups, and also serves to keep the metal oxides dispersed from each other. The polymer can be a synthetic polymer, such as, but not limited to, polyethylene glycol or silane, natural polymers, or derivatives of either synthetic or natural polymers or a combination of these. Useful polymers are hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, carboxydextran, carboxymethyl dextran, and/or reduced carboxymethyl dextran. The metal oxide can be a collection of one or more crystals that contact each other, or that are individually entrapped or surrounded by the polymer.

In other embodiments, the nanoparticles are associated with non-polymeric functional group compositions. Methods are known to synthesize stabilized, functionalized nanoparticles without associated polymers, which are also within the scope of this invention. Such methods are described, for example, in Halbreich et al., *Biochimie,* 80 (5-6):379-90, 1998.

The nanoparticles have an overall size of less than about 1-100 nm. The metal oxides are crystals of about 1-25 nm, e.g., about 3-10 nm, or about 5 nm in diameter. The polymer component in some embodiments can be in the form of a coating, e.g., about 5 to 20 nm thick or more. The overall size of the nanoparticles is about 15 to 200 nm, e.g., about 20 to 100 nm, about 40 to 60 nm; or about 50 nm.

The conjugates have high relaxivity owing to the superparamagnetism of their iron or metal oxide. They have an R1 relaxivity between about 5 and 30 mM$^{-1}$ sec$^{-1}$, e.g., 10, 15, 20, or 25 mM$^{-1}$ sec$^{-1}$. They have an R2 relaxivity between about 15 and 100 mM$^{-1}$ sec$^{-1}$, e.g., 25, 50, 75, or 90 mM$^{-1}$ sec$^{-1}$. They typically have a ratio of R2 to R1 of between 1.5 and 4, e.g., 2, 2.5, or 3. They typically have an iron oxide content that is greater than about 10% of the total mass of the particle, e.g., greater than 15, 20, 25 or 30 percent.

Synthesis of Nanoparticles

There are varieties of ways that the nanoparticles can be prepared, but in all methods, the result must be a nanoparticle with functional groups that can be used to link the nanoparticle to the binding moiety.

For example, oligonucleotide binding moieties can be linked to the metal oxide through covalent attachment to a functionalized polymer or to non-polymeric surface-functionalized metal oxides. In the latter method, the nanoparticles can be synthesized according to the method of Albrecht et al., Biochimie, 80 (5-6): 379-90, 1998. Dimercapto-succinic acid is coupled to the iron oxide and provides a carboxyl functional group. By functionalized is meant the presence of amino or carboxyl or other reactive groups (see, Table 1, which is described in further detail below).

In another embodiment, oligonucleotides are attached to magnetic nanoparticles via a functionalized polymer associated with the metal oxide. In some embodiments, the polymer is hydrophilic. In a specific embodiment, the conjugates are made using oligonucleotides that have terminal amino, sulfhydryl, or phosphate groups, and superparamagnetic iron oxide nanoparticles bearing amino or carboxy groups on a hydrophilic polymer. There are several methods for synthesizing carboxy and amino derivatized-nanoparticles. Methods for synthesizing functionalized, coated nanoparticles are discussed in further detail below.

Carboxy functionalized nanoparticles can be made, for example, according to the method of Gorman (see WO 00/61191). In this method, reduced carboxymethyl (CM) dextran is synthesized from commercial dextran. The CM-dextran and iron salts are mixed together and are then neutralized with ammonium hydroxide. The resulting carboxy functionalized nanoparticles can be used for coupling amino functionalized oligonucleotides, see Table 1.

Carboxy-functionalized nanoparticles can also be made from polysaccharide coated nanoparticles by reaction with bromo or chloroacetic acid in strong base to attach carboxyl groups. In addition, carboxy-functionalized particles can be made from amino-functionalized nanoparticles by converting amino to carboxy groups by the use of reagents such as succinic anhydride or maleic anhydride.

Nanoparticle size can be controlled by adjusting reaction conditions, for example, by using low temperature during the neutralization of iron salts with a base as described in U.S. Pat. No. 5,262,176. Uniform particle size materials can also be made by fractionating the particles using centrifugation, ultrafiltration, or gel filtration, as described, for example in U.S. Pat. No. 5,492,814.

Nanoparticles can also be synthesized according to the method of Molday (Molday, R. S, and D. MacKenzie, "*Immunospecific ferromagnetic iron-dextran reagents for the labeling and magnetic separation of cells*," J. Immunol. Methods, 1982, 52(3):353-67, and treated with periodate to form aldehyde groups. The aldehyde-containing nanoparticles can then be reacted with a diamine (e.g., ethylene diamine or hexanediamine), which will form a Schiff base, followed by reduction with sodium borohydride or sodium cyanoborohydride.

Dextran-coated nanoparticles can be made and cross-linked with epichlorohydrin. The addition of ammonia will react with epoxy groups to generate amine groups, see Hogemann, D., et al., *Improvement of MRI probes to allow efficient detection of gene expression* Bioconjug. Chem. 2000. 11(6): 941-6, and Josephson et al., "*High-efficiency intracellular magnetic labeling with novel superparamagnetic-Tat peptide conjugates*," Bioconjug. Chem., 1999, 10(2):186-91. This material is known as cross-linked iron oxide or "CLIO" and when functionalized with amine is referred to as amine-CLIO or NH$_2$—CLIO.

Carboxy-functionalized nanoparticles can be converted to amino-functionalized magnetic particles by the use of water-soluble carbodiimides and diamines such as ethylene diamine or hexane diamine.

Avidin or streptavidin can be attached to nanoparticles for use with a biotinylated binding moiety, such as an oligonucleotide or polypeptide. See e.g., Shen et al., "*Magnetically labeled secretin retains receptor affinity to pancreas acinar cells*," Bioconjug. Chem., 1996, 7(3):311-6. Similarly, biotin can be attached to a nanoparticle for use with an avidin-labeled binding moiety.

In all of these methods, low molecular weight compounds can be separated from the nanoparticles by ultra-filtration, dialysis, magnetic separation, or other means. The unreacted oligonucleotides can be separated from the oligonucleotide-nanoparticle conjugates, e.g., by magnetic separation or size exclusion chromatography.

Binding Moieties

The binding moiety is a molecule, synthetic or natural, that specifically binds to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target molecule such as enzyme in solution.

Oligonucleotide Binding Moieties

In certain embodiments, the binding moieties are oligonucleotides, attached to the nanoparticles using any one of a variety of chemistries, by a single, e.g., covalent, bond, e.g., at the 3' or 5' end to a functional group on the nanoparticle.

The new conjugates are useful in various types of MR applications, including but not limited to, in vitro methods for assaying the presence or concentration of nucleic acids, and in vivo methods as MR imaging agents.

An oligonucleotide binding moiety of the invention can be constructed using chemical synthesis. A double-stranded DNA binding moiety can be constructed by enzymatic ligation reactions using procedures known in the art. For example, a nucleic acid (e.g., an oligonucleotide) can be chemically synthesized using naturally occurring nucleotides or variously modified nucleotides designed to increase the biological stability of the molecules or to increase the physical stability of the duplex formed between the complementary strands, e.g., phosphorothioate derivatives and acridine substituted nucleotides can be used. The nucleic acid also can be produced biologically using an expression vector into which a nucleic acid has been subcloned.

One of the new in vitro assay methods uses at least two populations of oligonucleotide magnetic nanoparticles, each with strong effects on water relaxation (see Table 2). As the oligonucleotide-nanoparticle conjugates react with a target oligonucleotide, they form aggregates (100-500 nm; aggregates were 215 nm in size in Table 2). Upon prolonged standing, e.g., overnight at room temperature, the aggregates form large clusters (micron-sized particles), which settle out of solution, see FIG. 2B. The invention uses magnetic resonance to determine the relaxation properties of the solvent, which are altered when the mixture of magnetic oligonucleotide nanoparticles reacts with a target nucleic acid to form aggregates.

A feature of the analytical method when using oligonucleotide binding moieties is the need for a mixture of at least two types of magnetic metal oxide nanoparticles, each with a specific sequence of oligonucleotide, and each with more than one copy of the oligonucleotide attached, e.g., covalently, per nanoparticle. The assay protocol involves preparing a mixture of populations of oligonucleotide-nanoparticle conjugates and reacting the mixture with a target nucleic acid. Alternatively, oligonucleotide-nanoparticle conjugates can be reacted with the target in a sequential fashion. A second feature of the new analytical method is the use of magnetic resonance to detect the reaction of the oligonucleotide-nanoparticle conjugates with the target nucleic acid. When a target is present, the dispersed conjugates self-assemble to form small aggregates.

Synthesis of Oligonucleotides

The oligonucleotides used to make the conjugates are preferably deoxyribonucleotides. Ribose-based oligonucleotides can also be use used, provided care is taken to eliminate RNA digesting enzymes. The oligonucleotide can be synthesized with a single reactive group at the 3' or 5' end, as indicated in Table 1, by methods known in the art. The reactive group at the 3' or 5' end insures covalent attachment on one end of the oligonucleotide. These can have 3' or 5' amino, phosphate, or sulfhydryl groups. One useful method, as described in Example 2, includes the use of 5'-alkanethiol-oligonucleotide and 3'-alkanethiol-oligonucleotides. Oligonucleotides can be obtained from numerous commercial sources. Alternatively, oligonucleotides with biotin attached at the 3' or 5' end can be synthesized by methods known in the art, and used in conjunction with an avidin-bound nanoparticle.

Polypeptide Binding Moieties

In certain embodiments, the binding moiety is a polypeptide (i.e., a protein, polypeptide, or peptide), attached, using any of a variety of chemistries, by a single covalent bond in such a manner so as to not affect the biological activity of the polypeptide. In one embodiment, attachment is done through the thiol group of single reactive cysteine residue so placed that its modification does not affect the biological activity of the polypeptide. In this regard the use of linear polypeptides, with cysteine at the C-terminal or N-terminal end, provides a single thiol in a manner similar to which alkanethiol supplies a thiol group at the 3' or 5' end of an oligonucleotide. Similar bifunctional conjugation reagents, such as SPDP and reacting with the amino group of the nanoparticle and thiol group of the polypeptide, can be used with any thiol bearing binding moiety. The types of polypeptides used as binding moieties can be antibodies, antibody fragments, and natural and synthetic polypeptide sequences. In all embodiments, these peptide binding moieties must have a binding partner, a molecule to which they selectively bind.

Use of peptides as binding moieties offers several advantages: First, the mass per binding site is low. For example, up to twenty 2 kDa peptides can be attached to a nanoparticle, calculated assuming 2064 iron atoms per nanoparticle. With larger binding moieties like proteins (generally greater than about 30 kDa) the same mass of attached polypeptide results in only approximately 1-4 binding moieties per nanoparticle. Second, polypeptides can be engineered to have uniquely reactive residues, distal from the residues required for biological activity, for attachment to the nanoparticle. The reactive residue can be a cysteine thiol, an N-terminal amino group, a C-terminal carboxyl group or a carboxyl group of aspartate or glutamate, etc. A single reactive residue on the peptide is used to insure a unique site of attachment. These design principles can be followed with chemically synthesized peptides or biologically produced polypeptides.

The binding moieties can also contain amino acid sequences from naturally occurring (wild-type) polypeptides or proteins. For example, the natural polypeptide may be a hormone, (e.g., a cytokine, a growth factor), a serum protein, a viral protein (e.g., hemagglutinin), an extracellular matrix protein, a lectin, or an ectodomain of a cell surface protein. In each case, the resulting binding moiety-nanoparticle is used to measure the presence of analytes in a test media reacting with the binding moiety.

Examples of protein hormones include: platelet-derived growth factor (PDGF) which binds the PDGF receptor; insulin-like growth factor-I and -II (Igf) which binds the Igf receptor; nerve growth factor (NGF) which binds the NGF receptor; fibroblast growth factor (FGF) which binds the FGF receptor (e.g., aFGF and bFGF); epidermal growth factor (EGF) which binds the EGF receptor; transforming growth factor (TGF, e.g., TGF-α and TGF-β) which bind the TGF receptor; erythropoietin, which binds the erythropoitin receptor; growth hormone (e.g., human growth hormone) which binds the growth hormone receptor; and proinsulin, insulin, A-chain insulin, and B-chain insulin, which all bind to the insulin receptor.

Receptor binding moieties are useful for detecting and imaging receptor clustering on the surface of a cell.

Useful ectodomains include those of the Notch protein, Delta protein, integrins, cadherins, and other cell adhesion molecules.

Polypeptide Synthesis

Methods for synthesizing polypeptides in solution are well established in the field. Solid-phase peptide synthesis (SPPS) can be used effectively to produce peptides and small proteins of specific sequences for use in the present invention.

The concept of the solid-phase approach involves covalent attachment (anchoring) of the growing peptide chain to an insoluble polymeric support (resin carrier), so that unreacted soluble reagents can be removed by simple filtration and washing without manipulative losses. Subsequently, the insoluble peptide-resin is extended by a series of additional cycles, which are required to proceed with high yields and fidelities. Excess soluble reagents are used to drive reactions to completion. Because of the speed and simplicity of the repeated steps, the major portion of the solid-phase procedure is amenable to automation. Once chain elaboration has been accomplished, it is necessary to release (cleave) the crude peptide from the support under conditions that are minimally destructive towards sensitive residues in the sequence.

Antibody Binding Moieties

Other polypeptide binding moieties include immunoglobulin binding moieties that include at least one immunoglobulin domain, and typically at least two such domains. An "immunoglobulin domain" refers to a domain of a antibody molecule, e.g., a variable or constant domain. An "immunoglobulin superfamily domain" refers to a domain that has a three-dimensional structure related to an immunoglobulin domain, but is from a non-immunoglobulin molecule. Immunoglobulin domains and immunoglobulin superfamily domains typically include two β-sheets formed of about seven β-strands, and a conserved disulphide bond (see, e.g., Williams and Barclay 1988 *Ann. Rev Immunol.* 6:381-405).

Proteins that include domains of the Ig superfamily domains include T cell receptors, CD4, platelet derived growth factor receptor (PDGFR), and intercellular adhesion molecule (ICAM).

One type of immunoglobulin binding moiety is an antibody. The term "antibody," as used herein, refers to a full-length, two-chain immunoglobulin molecule and an antigen-binding portion and fragments thereof, including synthetic variants. A typical antibody includes two heavy (H) chain variable regions (abbreviated herein as VH), and two light (L) chain variable regions (abbreviated herein as VL). The VH and VL regions can be further subdivided into regions of hypervariability, termed "complementarity determining regions" (CDR), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917). Each VH and VL is composed of three CDR's and four FRs, arranged from amino-terminus to carboxy-terminus in the following order: FR1, CDR1, FR2, CDR2, FR3, CDR3, FR4.

An antibody can also include a constant region as part of a light or heavy chain. Light chains can include a kappa or lambda constant region gene at the COOH-terminus (termed CL). Heavy chains can include, for example, a gamma constant region (IgG1, IgG2, IgG3, IgG4; encoding about 330 amino acids). A gamma constant region can include, e.g., CH1, CH2, and CH3. The term "full-length antibody" refers to a protein that includes one polypeptide that includes VL and CL, and a second polypeptide that includes VH, CH1, CH2, and CH3.

The term "antigen-binding fragment" of an antibody, as used herein, refers to one or more fragments of a full-length antibody that retain the ability to specifically bind to a target. Examples of antigen-binding fragments include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment."

Antibody Production and Isolation

Typically, an immunoglobulin binding moiety is monospecific. Monospecific antibodies can be obtained by cloning and expressing antibody genes, e.g., from a monoclonal antibody cDNA. Also, polyclonal antibodies can be generated by immunization of, e.g., a horse, goat, rabbit, sheep, with an antigen. Production of antibodies and antibody fragments is well documented in the field. See, e.g., Harlow and Lane, 1988. Antibodies, A Laboratory Manual. Cold Spring Harbor, N.Y.: Cold Spring Harbor Laboratory. For example, Jones et al., Nature 321: 522-525 (1986), which discloses replacing the CDRs of a human antibody with those from a mouse antibody. Marx, Science 229: 455-456 (1985), discusses chimeric antibodies having mouse variable regions and human constant regions. Rodwell, Nature 342: 99-100 (1989), discusses lower molecular weight recognition elements derived from antibody CDR information. Clackson, Br. J. Rheumatol. 3052: 36-39 (1991), discusses genetically engineered monoclonal antibodies, including Fv fragment derivatives, single chain antibodies, fusion proteins chimeric antibodies and humanized rodent antibodies. Reichman et al., Nature 332: 323-327 (1988) discloses a human antibody on which rat hypervariable regions have been grafted. Verhoeyen, et al., Science 239: 1534-1536 (1988), teaches grafting of a mouse antigen binding site onto a human antibody.

Polysaccharide Binding Moieties

In certain embodiments, the binding moiety is a polysaccharide, linked, using any of a variety of chemistries, by a single bond, e.g., a covalent bond, at one of the two ends, to a functional group on the nanoparticle. The polysaccharides can be synthetic or natural. Mono-, di-, tri- and polysaccharides can be used as the binding moiety. These include, e.g., glycosides, N-glycosylamines, O-acyl derivatives, O-methyl derivatives, osazones, sugar alcohols, sugar acids, sugar phosphates when used with appropriate attachment chemistry to the nanoparticle.

A generally useful method of accomplishing linking is to couple avidin to a magnetic nanoparticle and react the avidin-nanoparticle with commercially available biotinylated polysaccharides, to yield polysaccharide-nanoparticle conjugates. For example, sialyl Lewis based polysaccharides are commercially available as biotinylated reagents and will react with avidin-CLIO (see Syntesome, Gesellschaft für medizinische Biochemie mbH.). The sialyl Lewis x tetrasaccharide (Sle$^x$) is recognized by proteins known as selectins, which are present on the surfaces of leukocytes and function as part of the inflammatory cascade for the recruitment of leukocytes.

Still other targeting moieties include a non-proteinaceous element, e.g., a glycosyl modification (such as a Lewis antigen) or another non-proteinaceous organic molecule.

Polysaccharide Isolation

Bacterial membrane-attached polysaccharide can be purified, for example, from the SKU 1100 strain by cell disruptions using either ultrasonic treatment or lysozyme treatment, followed by ultracentrifugation, enzyme treatments, dialysis against SDS, DEAE-cellulose column chromatography, alcohol precipitation, and gel filtration chromatography.

Polysaccharides can also be synthesized and are commercially available.

Coupling of Binding Moieties to Nanoparticles to Prepare Conjugates

The conjugates are prepared by linking two or more binding moieties to each magnetic nanoparticle. A general procedure for synthesizing amino-cross linked iron oxide nanoparticle begins with the synthesis of a dextran coated superparamagnetic iron oxide. There are a variety of satisfactory procedures which can employed such as those in Weissleder "Monocrystalline iron oxide particles for studying biological tissues" U.S. Pat. No. 5,492,814; Molday, R. S, and D. MacKenzie, "Immunospecific ferromagnetic iron-dextran reagents for the labeling and magnetic separation of cells," J. Immunol. Methods, 1982, 52(3):353-67, Palmacci "Synthesis of Polysaccharide Coated Superparamagnetic Oxide Colloids," U.S. Pat. No. 5,262,176.

For example, a pure dextran coated superparamagnetic iron oxide can be reacted with a crosslinking agent such as 5-50% epichlorohydrin or epibromohydrin in strong base (final concentration 1-3 M NaOH). After a sufficient time at room temperature, liquid ammonia in excess is added to aminate the polysaccharide. Low molecular weight impurities are removed, e.g., by centrifugation or exhaustive ultrafiltration using a membrane with a 10 kDa cutoff.

Coupling of Oligonucleotides to Nanoparticles

The invention provides for preparing oligonucleotides with reactive 3', 5', or both termini. One terminus is attached to the surface of the nanoparticle, leaving the other terminus free for attachment to another molecule, e.g., a biotin group or another tag.

Table 1 provides a partial list of techniques and reagents that can be used to couple oligonucleotides to amino- or carboxy-functionalized nanoparticles. The general strategy is to provide an oligonucleotide with a unique reactive group on the 3' or 5' end. Exemplary groups include sulfhydryl, amino, and phosphate groups. Oligonucleotides with sulfhydryl groups at the 3' or 5' end are of particular value, and are commercially available. They can be coupled to amino-nanoparticles through the use of reagents such as N-succinimidyl 3-(2-pyridyldithio)propionate (SPDP) and long chain SPDP (lc-SPDP) that produce a cleavable disulfide bond between the nanoparticle and the oligonucleotide. Amino-nanoparticles can also be reacted with reagents such as succinimidyl-iodoacetate to produce non-cleavable bonds between the nanoparticle and oligonucleotide.

TABLE 1

Functional Groups and Strategies for coupling oligonucleotides to nanoparticles

| Oligonucleotide Terminal Group | Nanoparticle Functional Group | Coupling Chemistry | Cleavable |
|---|---|---|---|
| Sulfhydryl | Amino | SPDP, lc-SPDP (lc, long chain) | Yes |
| Sulfhydryl | Amino | Succinimidyl-iodoacetate | No |
| Amino | Carboxyl | CDI (carbodiimide) | No |
| Phosphate | Amino | CDI | No |
| Biotin | Avidin | Not applicable | Not applicable |

Thus, nanoparticles can be conjugated to oligonucleotides through a variety of conjugation chemistries. See U.S. Pat. No. 5,512,439; Greg Hernanson "Bioconjugate Techniques," Academic Press, 1996; Gordon Bickerstaff "Immobilization of Enzymes and Cells," Humana Press, 1997. If a colloid containing a variety of sizes results, particles can be fractionated according to size, e.g., by ultrafiltration.

Non-polymeric surface functionalized metal oxides are coupled to oligonucleotides using coupling chemistries as shown, for example, in Table 1.

In other embodiments, populations of nanoparticle conjugates can be synthesized by allowing biotinylated oligonucleotides, polypeptides, or polysaccharides, to react with avidin (or streptavidin)-bound nanoparticles. Here a non-covalent, but tight, bond between the biotinylated binding moiety, e.g., oligonucleotide, and avidin of the nanoparticle attaches the oligonucleotide to the nanoparticle. Oligonucleotide-nanoparticle conjugate populations prepared in this fashion are analogous to those prepared with covalent chemistries (Table 1), and can be reacted with target oligonucleotides. Specific binding ligand pairs other than avidin-biotin are well known, and can also be used, e.g., fluorescein and antibodies specific for fluorescein, peptide hormones and their receptors, and steroids and their receptors, as long as they do not interfere with the function of the binding moieties.

An alternative protocol involves allowing two biotinylated oligonucleotides to react with (e.g., hybridize to) a target oligonucleotide. Following this reaction, a cross-linked iron oxide (CLIO) particle linked to avidin or streptavidin is added. The presence of the target nucleotide again results in the formation of aggregates and changes in T2. In this case, two populations of oligonucleotide-nanoparticle conjugates are formed when the avidin-nanoparticle is reacted with two biotinylated oligonucleotides. An advantage of this indirect capture method is that the biotinylated oligonucleotides that react with a target oligonucleotide are far smaller, and hence react faster, than oligonucleotide-nanoparticle conjugates. Biotinylated-oligonucleotides have molecular weights less than 50 kDa, while oligonucleotide-nanoparticle conjugates have molecular weights greater than about 1000 kDa (e.g., 1000, 2000, 3500, 5000, or more up to about 10,000 kD).

An alternative to the avidin-biotin system is the use of two-dye labeled oligonucleotides, which hybridize to a target oligonucleotide. An antibody to the dye coupled to a CLIO is then added.

Coupling of Polypeptides and Antibodies to Nanoparticles

The invention provides for preparing polypeptides with reactive 3', 5', or both termini. One end is linked to the surface of the nanoparticle, leaving the other end free for attachment to another molecule, e.g., a biotin group or another tag.

The conjugation of polypeptides to nanoparticles can be accomplished by a large number of conjugation chemistries and reagents some of which are also used for attaching oligonucleotides to nanoparticles, see Table 1. A preferred general strategy is to use one of the large number of bifunctional agents that can be reacted first with the amino group of the nanoparticle, and secondly with the thiol group of the polypeptide (or biomolecule). Examples of such bifunctional reagents are SPDP, MBS, lc-SPDP and SMCC and are available from companies, e.g., Pierce Chemical, Molecular Probes or Molecular Biosciences. The bifunctional agent is dissolved in DMSO and reacted in excess with the amino functionalized nanoparticle at pH 8 using a non-amine containing buffer (e.g., borate, phosphate). Unreacted bifunctional agent is removed by dialysis, ultrafiltration, gel permeation chromatography or by using magnetic filters. The sulfhydryl bearing polypeptide (biomolecule) is then added and allowed to react. Unreacted polypeptide can be removed by the separation methods above. For details see Josephson et al, (1999) High-efficiency intracellular magnetic labeling with novel superparamagnetic-Tat peptide conjugates, *Bioconjugate Chemistry*, 10, 186-91; Perez et al. (2002) DNA-based magnetic nanoparticle assembly acts as a magnetic relaxation nanoswitch allowing screening of DNA-cleaving agents, *Journal of the American Chemical Society*, 124, 2856-2857; Kang et al. (2002) Magnetic Resonance Imaging of Inducible E-Selectin Expression in Human Endothelial Cell Culture, *Bioconjugate Chemistry*, 13, 122-127; Hoegemann et al, (2000) Improvement of MRI Probes To Allow Efficient Detection of Gene Expression, *Bioconjugate Chemistry*, 11, 941-946. Detailed protocols are also available from the manufacturers.

In one embodiment, the conjugate can be synthesized by allowing a biotinylated antibody or antibody fragment to react with avidin (or streptavidin) nanoparticles. Here a non-covalent, but tight, bond between the biotinylated antibody and avidin of the nanoparticle attaches the antibody to the nanoparticle.

In another embodiment, a natural or synthetic polypeptide is covalently or non-covalently attached to the nanoparticle while the other terminal is biotinylated.

In one aspect of the invention, both ends of the polypeptide are biotinylated and avidin is directly attached to the nanoparticle.

In another embodiment, both termini of the peptide are covalently or non-covalently attached to two nanoparticles.

Coupling of Polysaccharides to Nanoparticles

The invention provides for preparing polysaccharides with reactive ends. One end is attached to the surface of the nanoparticle, leaving the other end free for attachment to another molecule. For example, as described above, the free end of the polysaccharide can be biotinylated and aggregation can be induced by exposure to avidin. Also, the polysaccharide can be biotinylated on both termini and exposed to avidin linked to a nanoparticle.

Characterizing Conjugates

The conjugates can form several conformations, or "states," in solution. The first is the monodispersed conformation, represented when a binding moiety of a conjugate has not reacted with a target molecule. This conformation is approximately 4-100 nm (e.g., 5, 10, 25, 40, 50, 75, or 90 nm) in size.

The second conformation is a small aggregate, which contains 2 to about 20 (e.g., 3, 5, 7, 10, 15, or 20) individual nanoparticle conjugates held together by the interaction (e.g., binding) of the binding moiety with a target, or with another binding moiety. The association of the nanoparticles is mediated by the attached biomolecules and not by nanoparticle non-specific attractions. This aggregate is approximately 100-500 nm (e.g., 200, 250, 300, or 400 nm) in size, is stable, and remains in solution. The metal oxide, e.g., iron oxide, concentration used to form the small aggregate is about 1-25, e.g., 5-20 µg/ml. The small aggregates do not settle out of solution and are "porous" in that they do not sterically block large molecules (e.g., enzymes) from entering the aggregate. The "pores" are really spaces or openings between the binding moieties that combine to form the aggregates, which can be envisioned as a three-dimensional lattice or mesh. The size of the openings can be controlled by adjusting the size of the nanoparticles and the size of the binding moieties on each conjugate. The small aggregates are stable under a variety of conditions, e.g., stable from 4° C. to 80° C., stable in denaturants, stable in high salts, and is stable at a pH varying from about 5.5 to 14.

The third conformation is the large aggregate cluster, which is, in effect, an aggregate of aggregates. The cluster contains greater than 20 nanoparticles and is greater than 500 nm in size. The cluster is not useful since it typically clumps and falls out of solution.

The nanoparticle conjugates can be used as magnetic nanosensors or magnetic relaxation switches (MRS) in various detection systems. For example, the new methods can utilize detectors that measure the magnetic properties of the conjugates and aggregates (e.g., magnetometers, oscillating magnetic field readers, and superconducting quantum interference device (SQUID) detectors). Other detection methods include magnetic force microscopy or atomic force microscopy, flow cytometry, centrifugation, light scattering, and size separation.

In magnetic resonance (MR) imaging applications, the novel conjugates provide methods for the detection and a spatial localization of specific sequences of target molecules, such as nucleic acids, in living systems. This is based on the remarkable ability of the magnetic conjugates to effect water relaxation in a sequence specific manner even in media that will not permit assays using light-based methods of gene detection (see Example 5). Hence, the new conjugates can function as MR contrast agents for the detection of target molecules, such as nucleic acids and polypeptides in vivo.

The new conjugates are essentially nontoxic to mammalian cells. In one embodiment, non-degradable oligonucleotide analogs (e.g., peptide nucleic acid or PNA) may be coupled to nanoparticles and used to image sequences of nucleic acids in vivo. Nontoxicity is evident from the use of magnetic nanoparticles as the active ingredient of COMBIDEX®, a nanoparticle-based MR contrast agent, which has been judged approvable by the FDA (January 1999). COMBIDEX® is similar to MION (monodisperse iron oxide nanospheres). MION is a starting material for aminated CLIO used in one embodiment herein (see FIG. 1.). Thus, the new conjugates and aggregates can be administered to a subject, e.g., a human or animal, such as a mammal (e.g., dogs, cats, cows, pigs, and horses). Various routes of administration can be used to achieve systemic or local delivery. Because of the specific binding characteristics Oligonucleotide Conjugates The starting material used in some of the examples described herein consists of monodisperse or polydisperse, fluid-phase nanoparticles containing superparamagnetic $Fe_2O_3/Fe_3O_4$ (3-5 nm), caged by epichlorohydrin cross-linked dextran, and functionalized with amine groups ($NH_2$—CLIO). Thiolated oligonucleotides were coupled to $NH_2$—CLIO using N-succinimidyl 3-(2-pyridyldithio)propionate (SPDP) as a linker (FIG. 1). The physical properties of the conjugates P1 (CLIO-SS-(($CH_2$)$_6$—CGC-ATT-CAG-GAT) (SEQ ID NO:1)) and P2 ((TCT-CAA-CTC-GTA-(SEQ ID NO:2)($CH_2$)$_3$)—SS-CLIO) are summarized in Table 2. P1 and P2 each had an average of 3 oligonucleotides per particle based on a single crystal per particle and 2064 iron atoms per crystal (see Shen reference above). They could be stored at room temperature or 4° C. for several months without precipitation.

To effect maximum detection of target oligonucleotide sequence, hybridization conditions are established by methods well known in the art. Hybridization of the oligonucleotide-nanoparticle conjugates to the target nucleic acids is typically performed under moderate to high stringency conditions. The parameters of salt concentration and temperature, which affect stringency of hybridization, can be varied to achieve the optimal level of identity between the base sequences of the oligonucleotide-nanoparticle conjugates and those of the target oligonucleotide or nucleic acid being detected. These techniques and methods are well-known in the field. Additional guidance regarding such conditions is available, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

For example, if stringent hybridization conditions are desired, one can perform hybridization in 6× sodium chloride/sodium citrate (SSC) at about 45° C., followed by one or more washes in 0.2×SSC, 0.1% SDS at 50° C. Another example of stringent hybridization conditions is hybridization in 6×SSC at about 45° C., followed by one or more washes in 0.2×SSC, 0.1% SDS at 55° C. A further example of stringent hybridization conditions is hybridization in 6×SSC at about 45° C., followed by one or more washes in 0.2×SSC, 0.1% SDS at 60° C. Other stringency conditions are 0.5M sodium phosphate, 7% SDS at 65° C., followed by one or more washes at 0.2×SSC, 1% SDS at 65° C.

To demonstrate the ability of P1 and P2 to hybridize to a target oligonucleotide, P1/P2 mixtures were incubated with a complementary oligonucleotide. The samples became slightly turbid within 3-4 hours at room temperature, with a brown precipitate forming after 16 hours (FIG. 2B). The precipitate in the vial shown in FIG. 2B was moved to the side with a hand held magnet. Tubes containing the P1/P2 mixture alone, the P1 with complementary oligonucleotide, or the P1/P2 mixture with half-complementary oligonucleotide did not show turbidity or precipitate formation even after weeks at room temperature (FIGS. 2A, 2C, and 2D).

To further elucidate the interaction of P1/P2 with complementary oligonucleotide, gel electrophoresis was performed. Under non-denaturing conditions, and without DTT, the precipitate (as shown in the vial in FIG. 2B) remained at the top of the gel (FIG. 3A, lane 1). Treatment with DTT (FIG. 3A, lane 2) resulted in a single band of hybridized oligonucleotide. Under denaturing conditions and with DTT added (FIG. 3B), two bands were observed, the slower one consisting of complementary oligonucleotide and the faster one of a mixture of 3' and 5' oligonucleotides.

Figure 4:
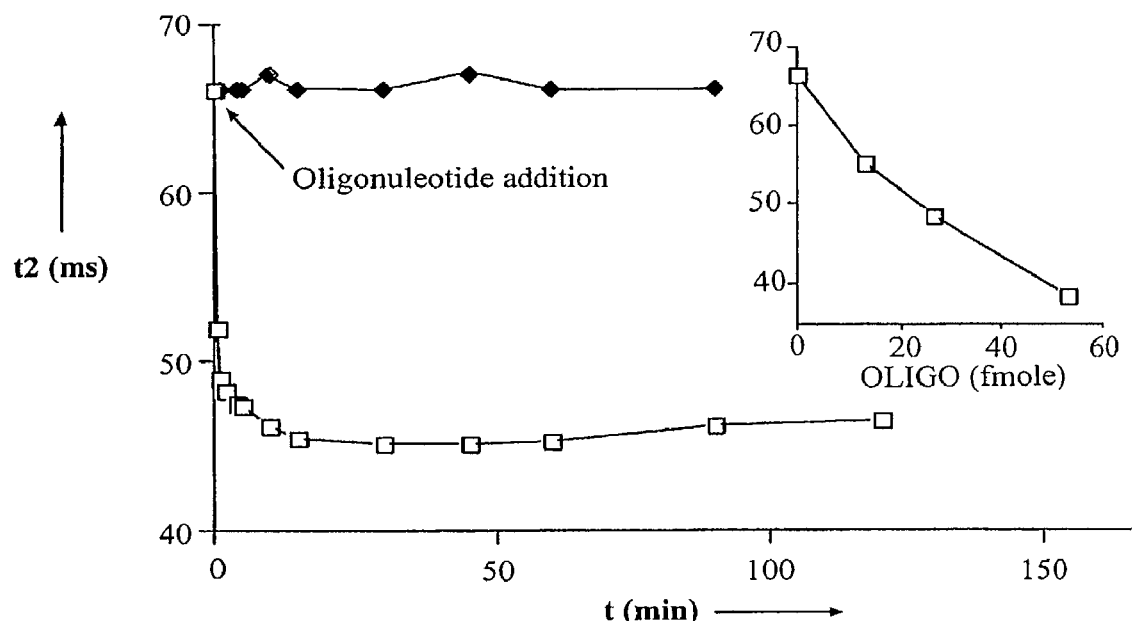
FIG. 4 is a graph illustrating the temporal change of water T2 relaxation times with (square) and without complementary oligonucleotide (diamond). The insert shows the effect of increasing concentrations of complementary oligonucleotide on T2. All data points shown represent the average of three measurements with standard deviations ranging between 0.4-0.6 msec for T2 values (too small to graph).

The nanoparticles P1 and P2 are potent enhancers of the spin-spin and spin-lattice relaxation processes (Table 2). Interestingly, the spin-spin relaxation was furthermore significantly enhanced by oligonucleotide hybridization, rendering the particles as potential "magnetic nanosensors." FIG. 4 shows the effect of oligonucleotide addition to an aqueous solution of P1/P2. Within several minutes, T2 decreased from 63 ms to 45 ms and this effect persisted for the period of observation (2 hours). The insert in FIG. 4 plots the T2 decrease as a function of oligonucleotide added. Table 2 summarizes the concentration independent R1 and R2 relaxivities before and after hybridization. Hybridization primarily affected R2 with a doubling of the R2/R1 ratio. Concomitant laser light scattering indicated a significant size increase of hybridized conjugates, presumably causing effects on spin-spin relaxation.

differences in base pairing can be detected by T2 measurements (Table 3). Thus, the new conjugates are highly selective in binding to target molecules. For example, a single nucleotide insertion in the center of a target sequence can abrogate magnetic switching nearly completely. Similar effects are also seen with larger and other kinds of single and double inserts (Table 3).

To determine the effect that nucleotide mismatches could have on T2 measurements, additional target sequences containing both single and multiple mismatches were tested. Again, single nucleotide mismatches were detectable while double mismatches completely abrogated magnetic switching (Table 3).

TABLE 3

Summary of tested oligonucleotide sequences and magnetic measurements

| | ∂T2 (msec)* | Deviation from normal** | p-value |
|---|---|---|---|
| Perfect match | | | |
| TAC-GAG-TTG-AGA-ATC-CTG-AAT-GCG SEQ ID NO:3 | 30 ± 2 | NA (match) | NA |
| Insertions | | | |
| AC-GAG-TTG-AGA-G-ATC-CTG-AAT-GCG SEQ ID NO:4 | 5 ± 1 | 83% | 0.0001 |

TABLE 2

Size and relaxivities before and after hybridization with target oligonucleotides

| Compound | Hybridization | Size (nm) | R1** (sec$^{-1}$ mM$^{-1}$) | R2** (sec$^{-1}$ mM$^{1}$) | R2/R1 |
|---|---|---|---|---|---|
| P1 | No | 53 ± 11 | 27.7 ± 0.3 | 75 ± 2 | 2.7 ± 0.1 |
| P2 | No | 53 ± 11 | 26.7 ± 0.3 | 71 ± 10 | 2.6 ± 0.4 |
| P1 + P2 + oligo non-complement. | No | 65 ± 25 | 25.8 ± 0.4 | 67 ± 1 | 2.6 ± 0.1 |
| P1 + P2 + oligo complement. | Yes | 215 ± 19 | 23.0 ± 1.0 | 128 ± 3 | 5.6 ± 0.2 |

* Determined by gel electrophoresis
**Relaxivities (units of sec$^{-1}$ mM$^{-1}$) are the slopes of plots of relaxation rate (1/T, sec$^{-1}$) against nanosensor concentration (Fe, mM); values are plotted as means ± SD, n = 3. Size refers to the unimodal size distribution as determined by light scattering, mean ± SD, n = 6.

Figure 5:
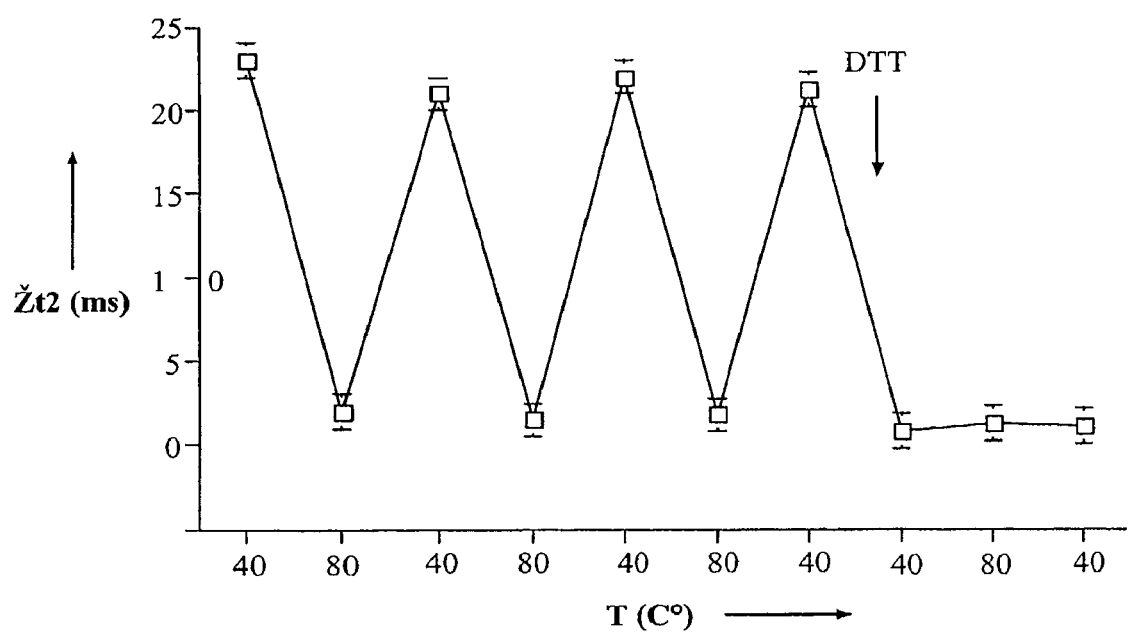
FIG. 5 is a graph illustrating the T2 changes of an aqueous solution of P1/P2/complementary oligonucleotide as a function of temperature cycling. T2 is different between two solutions of P1/P2, one with complementary and without complementary oligonucleotide. At 80° C. there is no hybridization and a very small difference in T2 values.

The effect of temperature cycling on the hybridization of the oligonucleotide nanoparticle was investigated by measuring changes in T2 values (FIG. 5). At 80° C., hybridization was minimal and T2 changes were small. During multiple cycles of heating and cooling representative T2 changes were observed. Furthermore, upon addition of DTT, oligonucleotides were cleaved from the nanoparticles and T2 did not change during further temperature cycling. These results indicate that oligonucleotide hybridization efficiently changes the spin-spin relaxation time of water, that these effects occur within minutes, that the magnetic effects are fully reversible through the use of DTT.

Selectivity

A unique feature of the magnetic nanoparticles is that they are highly stable to temperature fluctuations and to different ionic media. This stability enabled the use of buffer conditions (e.g. 25 mM KCl, 50 mM Tris, pH 7.5) in which small TABLE 3-continued Summary of tested oligonucleotide sequences and magnetic measurements

| | ∂T2 (msec)* | Deviation from normal** | p-value |
|---|---|---|---|
| TAC-GAG-TTG-AGA-GAG-TGC-ATC-CTG-AAT-GCG SEQ ID NO:5 | 2 ± 0.6 | 93% | 0.0001 |
| TAC-GAG-G-TTG-AGA-ATC-CTG-AAT-GCG SEQ ID NO:6 | 4 ± 2.5 | 87% | 0.0002 |
| TAC-GAG-G-TTG-AGA-ATC-CTG-G-AAT-GCG SEQ ID NO:7 | 2 ± 0.5 | 93% | 0.0001 |

TABLE 3-continued

Summary of tested oligonucleotide sequences
and magnetic measurements

|  | ∂T2 (msec)* | Deviation from normal** | p-value |
|---|---|---|---|
| Mismatches | | | |
| CTG-AAT-GCG TAC-GAG-TTG-AGA-CTC- SEQ ID NO:8 | 21 ± 1.2 | 30% | 0.0029 |
| GAC-GAG-TTG-AGA-ATC- CTG-AAT-GCG SEQ ID NO:9 | 21 ± 0.6 | 30% | 0.0020 |
| TAC-GAG-TTG-AGA-ATC- CTG-CAT-GCG SEQ ID NO:10 | 15 ± 0.6 | 50% | 0.0030 |
| TAC-GAG-TTG-AGA-CTC- CTC-AAT-GCG SEQ ID NO:11 | 1 ± 0.6 | 97% | 0.0001 |
| TAC-GAC-TTG-AGA-ATC- CTG-CAT-GCG SEQ ID NO:12 | 9 ± 1.7 | 70% | 0.0002 |

Figure 8B:
FIG. 8B is an MR image corresponding to the graph in FIG. 8A acquired 2 hours after hybridization indicating that T2 relaxation time measurements correlate with the fluorescence measurements
Figure 8A:
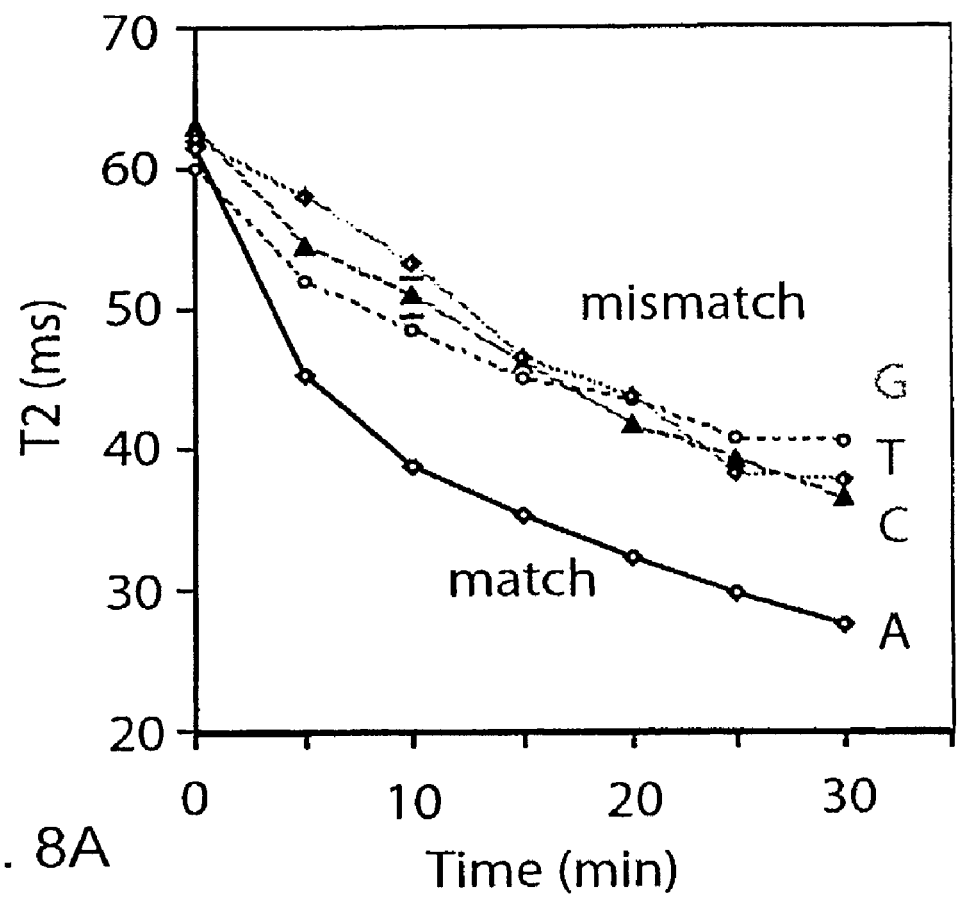
FIG. 8A is a graph depicting the specificity of magnetic nanosensors. Temporal change of T2 relaxation times of P1-GFP and P2-GFP with the addition of various target oligonucleotides containing single nucleotide mismatches G, T, C. The perfect target sequence is clearly distinguished from single nucleotide mismatches.

*∂T2 = $T2_{(t\ =\ 0\ min)} - T2_{(t\ =\ 30\ min)}$;
**deviation = $(\partial T2_{(perfect\ match)} - \partial T2_{(insertion\ or\ mismatch)})/\partial T2_{(perfect\ match)}) \times 100$ The selectivity of the MRS was further studied by preparing probes to target a GFP gene sequence and three variants with a single mismatch (T, C, G instead of an A). FIG. 8A shows the time course of T2 measurements with these four sequences. The perfect match (containing A) decreased T2 within minutes of oligonucleotide addition. The single mismatches behaved differently and these differences could be readily detected by T2 measurements at 40° C. As in the previous experiments, we also performed MR imaging at room temperature and were able to show similar differences (FIG. 8B). These data show that selective measurements capable of distinguishing single nucleotide mismatches can be carried out reliably and at various temperatures using either NMR or MRI techniques without the need for melting curve analysis.

Polypeptide Conjugates

Polypeptide conjugates behave in the same manner as the oligonucleotide conjugates, in that they are highly selective in their binding to target molecules and form aggregates as described further herein.

Uses of Binding Moiety-Nanoparticle Conjugates

The new conjugates can be used in two broad applications. In one application, the aggregate formation assay, a population of conjugates (or a mixture of two or more populations of conjugates with differing binding moieties directed to the same target molecule or type of target molecule) is placed into a sample solution. In this assay system, if the sample solution contains a target molecule to which the binding moieties specifically bind, the binding moieties interact with and bind to the target molecule resulting in the formation (self-assembly) of aggregates. As a result, the dispersed state of the conjugates switches to an aggregated state, which decreases T2 relaxation times. FIG. 1 depicts one embodiment of such an interaction in which two conjugates, P1 and P2, combine to form an aggregate of six conjugates.

In the other application, the aggregate dispersion assay, conjugates are used to prepare small aggregates, and the aggregates are placed into a sample solution. In this assay system, the binding moieties are designed so that they can be bound to each other (or to a specific aggregation inducing molecule, such as avidin) to form the aggregates, and to be (or form upon binding to each other or to the aggregation inducing molecule) a substrate that is cleaved by a specific target molecule. If the sample solution contains a target molecule, the substrate formed by the binding moieties is cleaved, resulting in the dissolution of the aggregates. Thus, the aggregated state switches to a dispersed state, which increases T2 relaxation times.

These aggregates can be observed and detected in vitro, e.g., in vials or arrays, e.g., 2-D or 3-D arrays, as well as in vivo, e.g., using MR imaging of a subject after administration of the conjugates or aggregates.

Aggregate Formation Assays

In this application, the conjugates must include binding moieties that specifically bind to at least two different binding sites or epitopes on the target molecule, and each conjugate must have at least two binding moieties. In general, the conjugates are added to a sample solution under conditions that enable the binding moieties to interact with and bind to the target molecule. As more of these interactions occur over time, several conjugates will accumulate together to form one aggregate. The endpoint of the assay is the detection of the presence of the aggregates, e.g., using MR imaging or other detection methods.

This application of the invention can be used in several assay systems. For example, when the binding moieties are nucleic acids, the new conjugates can be used for an analytic method referred to herein as the Hybridization Relaxation Assay System or HYRAS. Like the earlier SMRAS (Solvent Mediated Relaxation Assay System) technology (U.S. Pat. No. 5,164,297), HYRAS can be used to determine the concentration of an analyte in a sample by monitoring changes in a solvent relaxation rate. HYRAS differs from SMRAS in a number of important ways.

First, HYRAS involves the assay of nucleic acids using superparamagnetic iron oxide nanoparticles, and is based on the observation that nucleic acids do not non-specifically adsorb to iron oxides. This is surprising because the affinity between the iron on the surface of the iron oxide and phosphate or phosphate-containing compounds, such as nucleic acids, is strong. For example, iron oxides have been used to bind and extract DNA (see, e.g., examples 10 and 11 in U.S. Pat. No. 5,512,332). Thus, it is surprising that oligonucleotides, which contain a multiplicity of phosphate groups, do not interact non-specifically with the iron oxide nanoparticles.

Second, to produce the needed aggregation of nanoparticles by a specific target nucleotide, two types of oligonucleotide-nanoparticles are needed, each with a single type of oligonucleotide attached, each reacting with a different sequence present on a target complementary oligonucleotide (see FIG. 1). If two different oligonucleotides were coupled to the sample nanoparticle, the target nucleic acid would hybridize to the oligonucleotides on the same particle and no effect on water relaxation rates (T2) would result. SMRAS has no requirement for the synthesis of two different types of magnetic particles. Instead SMRAS uses multivalent proteins coupled to an iron oxide, which then reacts with multivalent proteins such as antibodies to produce changes in relaxation.

Third, in SMRAS and HYRAS particle aggregation alters T2 in opposite manners. For example, in SMRAS, the complex between BSA-coated magnetic particles and anti-BSA antibodies causes an increase in T2 (decrease in 1/T2); addition of BSA blocks this effect increasing 1/T2, see FIG. 4 of U.S. Pat. No. 5,164,297. In contrast, in HYRAS, when oligonucleotide-nanoparticles react with a target nucleotide to form aggregates there is a decrease in T2.

Fourth, the conjugation strategy used in HYRAS differs from that used in SMRAS. In HYRAS, oligonucleotides are attached to iron oxide colloid polymers with a single covalent bond at the 3' or 5' end of the oligonucleotide. This is essential because the oligonucleotides are sufficiently small (short), that if they were attached in the middle, and not by their 3' or 5' ends, they would not be able to hybridize to target nucleotides. In contrast, particles used in SMRAS, such as the dextran-coated iron oxide or BSA-coated iron oxide, are synthesized by the adsorption of polymers to the surface of the iron oxide. This attachment is maintained by a large number of non-covalent bonds.

The new methods can also be used to detect nucleic acids by magnetic resonance. This assay measures the presence of target oligonucleotides in turbid or tissue-like samples (see Example 5). This method provides advantages over light-based analytical methods, such as the non-magnetic, gold based calorimetric assays described in WO 98/04740. In one method using the gold nanoparticles, the color change is determined in solution, which requires a non-turbid, non-opaque solution. In a second method, oligonucleotide-gold conjugates are collected on an oligonucleotide bearing substrate, such as membrane or filter. Excess media, which interferes with the detection, is removed and amplification by a silver stain is employed. In the present invention, neither separation nor amplification steps are used. Instead, the presence of nanoparticle aggregate is detected by MR. The invention can be distinguished by the ability to "see" aggregate formation in highly turbid or opaque tissues by the use of magnetic resonance. This yields assays with reduced processing and handling steps.

Figure 6:
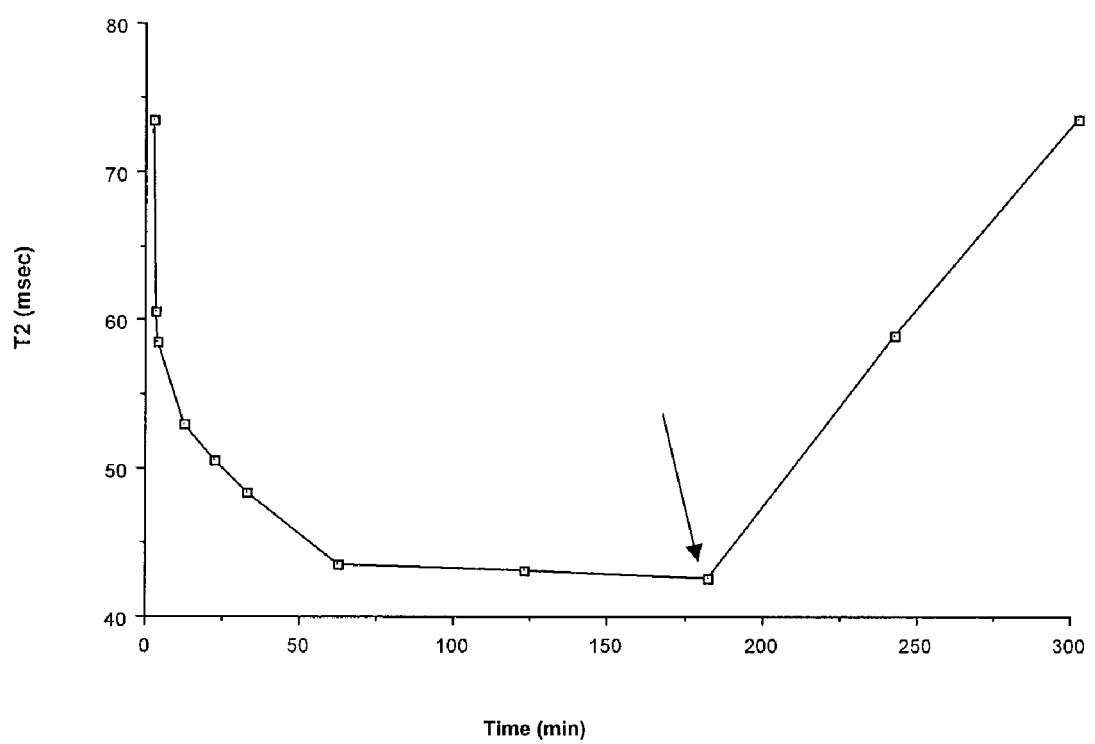
FIG. 6 is a graph showing T2 values of a turbid medium (INTRALIPID®) after a complementary oligonucleotide is added to an oligonucleotide nanoparticle conjugate mixture, P1 and P2. DTT was added after 180 minutes.

The novel conjugates of the invention can be used to measure the T2 values, and levels of oligonucleotides, in several samples simultaneously. This can be accomplished by replacing an MR spectrometer (FIGS. 4, 5 and 6 with an MR imager (FIG. 7). MR signal intensity was determined with a T2 weighted pulse sequence for a matrix of 24 wells of a 384 well microtiter plate. Further reduction in sample size, for example by the use of 1534 well microtiter plates, can be achieved. Microtiter plates can be stacked, and the capability of MR to measure the signal intensity of many slices, i.e., in three-dimensions, can be used to further increase assay throughput.

The new conjugates can also be used as MR contrast agents. In one embodiment, dextran coated superparamagnetic iron oxides (MION or COMBIDEX®) are synthesized (see U.S. Pat. No. 5,492,814 or 5,262,176) and then cross-linked and amino functionalized to yield $NH_2$—CLIO, as described herein. Alternatively, non-polymer coated iron oxide particles can be used. The nanoparticles are then coupled to specific oligonucleotides as shown, e.g., in FIG. 1. The resulting oligonucleotide-nanoparticle conjugates are then formulated in a physiologically acceptable media (e.g., saline or isotonic mannitol) and injected into an animal or human, intravenously at a dose between 0.1 and 10 mg Fe/kg. The contrast agent is permitted to accumulate in target tissue and is detected at highest sensitivity with T2 weighted spin-echo or gradient-echo pulse sequences.

In another example, detection of an mRNA in solution can be accomplished by synthesizing two populations of conjugates. The first contains an oligonucleotide sequence complementary to a sequence in the mRNA of interest and is bound at the 3' or 5' termini to the nanoparticle. A second conjugate is synthesized with a oligonucleotide sequence complementary to a different but proximate sequence of the mRNA. Addition of these conjugates to a solution containing the mRNA will result in the binding of the conjugates resulting in aggregation of the conjugates. Aggregation will produce a measurable decrease in the T2 by MR technology.

These novel conjugates can be used to determine the pattern of gene expression in a specimen (expression analysis) by extension of the methods shown in Example 6, below. Here a microtiter plate is prepared where each well contains different combinations of oligonucleotide-nanoparticles, i.e., combinations of oligonucleotides with different sequences attached to the same magnetic nanoparticle. The sequences of the oligonucleotides are chosen to permit hybridization, followed by aggregation and T2 change, with a unique target sequence that may or may not be present in the sample.

Another embodiment uses the same concept, but with proteins. For example, the conjugate can be used to detect the presence of an antigen in a sample. In this method, antibodies are linked covalently or non-covalently to the nanoparticle. To ensure that the antigen binding site is exposed, the C-terminus of the antibody or antibody fragment is attached to the nanoparticle. Monoclonal antibodies can be used for this method. A feature of this method is the need for a mixture of at least two types of nanoparticles, each with a specific binding moiety, e.g., monoclonal antibody attached. The antibodies are directed toward the same antigen, but recognize different determinants or epitopes. The populations are mixed in a sample and binding of the conjugate to an antigen induces aggregation, resulting in a measurable decrease in T2.

In another aspect of the invention, a polyclonal antibody can be attached to the nanoparticle. Since by definition these antibodies are multivalent, only a single population of conjugates is required.

Antibody fragments can also be used as long as they are bivalent. If single chain Fv fragments are used, there must be two populations of conjugates prepared. Each population will contain a single chain fragment directed to a distinct epitope of the same antigen.

These conjugates can also be used, as described above for the oligonucleotides, as magnetic nanosensors in other methods of antigen detection systems. These methods can utilize detectors that measure the magnetic properties of the particles (e.g., magnetometers, oscillating magnetic field readers, and superconducting quantum interference device (SQUID) detectors). Other detection methods include magnetic force microscopy or atomic force microscopy.

In the MR imaging application, the novel conjugates provide a method for the detection and a spatial localization of specific antigens in living systems. Hence antibody conjugates can function as MR contrast agents for the detection of polypeptides in vivo.

In another embodiment, conjugates can be useful in detecting a target molecule, e.g., an antibody, in solution. In this assay, the antigen will be bound to the nanoparticle and placed into a sample. If an antibody directed to the antigen is present, binding of the antigen will cause aggregation of the conjugate resulting on the decrease of T2. This assay method can be used for polyclonal and monoclonal antibodies and antibodies of any subclass because of the bivalent or polyvalent nature of the antibodies. This assay method can be used in the detection of antibodies, for example, in serum, acites fluid, cell culture medium, and cell lysates.

In another embodiment, the binding moiety can be a receptor-binding protein bound to the nanoparticle. When applied to a solution of cells, clustering of a cell surface receptor will result in aggregation of the conjugate followed by the concomitant decrease in T2. In another aspect of the invention, a kinase activity can be assayed. A peptide sequence with a serine or tyrosine kinase recognition site is attached to a nanoparticle at one terminal end. Addition of a solution containing a kinase will result in the phosphorylation of the binding moiety. Exposing the conjugates to anti-phosphotyrosine or anti-phosphoserine antibody will result in aggregation resulting the decrease of T2

Aggregate Dispersion Assays

In this application, a change in T2 is measured by preparing an aggregate of several conjugates, and then placing the aggregate into a solution (resulting in an immediate decrease in the T2), which may contain a target molecule. The aggregate is prepared by designing the binding moieties to form a substrate that is cleaved by the target molecule, thus dispersing the aggregates into conjugates, resulting in an increase of the T2 relaxation time. The binding moieties can bind to each other to form the substrate, or can contain the substrate, and form the aggregates by binding to an aggregation inducing molecule, such as avidin. The endpoint of the assay is the detection of the dissolution or dispersal of the aggregates (or the lack of formation of an aggregate if the target molecule and aggregate forming molecule are added to a solution of the conjugates at the same time).

In one embodiment, the new methods can be used to detect enzyme target molecules in a sample solution. The assay is based on the attachment to the nanoparticle of a natural or synthetic peptide that has an internal enzymatic site. Biotin is attached to the free terminus of the peptide. These biotin-labeled conjugates are mixed into a solution, and avidin (which binds four molecules of biotin per molecule of avidin) is added as the aggregation inducing molecule to form aggregates. These aggregates are then added to a sample solution. If there is a measurable increase in T2, then the enzyme is present. Alternatively, the conjugates can be added to a sample solution along with the avidin. If binding results in the aggregation of the conjugates, a measurable decrease in T2 can be observed, indicating that the target proteolytic enzyme is not present. However, if the enzyme is present and reacts with the substrate peptide in a relatively slow manner, a decrease in the T2 can be observed, followed by an increase of T2 when the aggregates are dispersed. If the reaction is fast, no decrease in T2 will be observed. This method can be used for any hydrolase that has a known recognition sequence.

In another variation of the invention, a peptide binding moiety containing an internal hydrolytic sequence can have biotin attached to both termini. Avidin is attached to the nanoparticles and mixed with the biotinylated peptide in a sample. Since one avidin molecule binds four biotin molecules, aggregation will occur if the biotinylated molecule is intact or if it has been cleaved. However, the degree of aggregation will be greater if the molecule is intact, therefore the sample will exhibit a greater degree of decreased T2.

In another aspect of the invention, immediate aggregation is induced by attaching a nanoparticle to both termini of the peptide. The conjugate is placed in the sample and the relaxivity is measured. If the enzyme of interest is present, then an increase in T2 will be measured when the peptide is cleaved.

The assay for the presence of a particular polysaccharidase can be accomplished in the same manner as described above for the enzyme assays using a polysaccharide as the binding moiety.

In another aspect of the invention, the conjugate can be used to detect a molecule that is transferred to the binding moiety. For example, DNA methyltransferase activity can be assayed. Hybridizing oligonucleotide conjugates can form a dam methylation site (GATC). The hybridization results in aggregation of the attached nanoparticle and a measurable decrease in T2. Upon contact with a methylase, the adenine and cytosine are methylated. Treatment with DpnI, a restriction endonuclease that specifically cleaves the methylated sequence GATC, results in dispersion of the aggregates followed by a measurable increase in T2.

In one aspect of the invention, oligonucleotide conjugates are synthesized to be complementary to each other. Upon hybridization of these conjugates in solution, the binding moieties form a double-stranded nucleic acid with a unique endonuclease restriction site (e.g., EcoRI, BamHI, PvuII). Hybridization of the oligonucleotides also aggregates the nanoparticles attached to the oligonucleotides resulting in a decreased T2. In this case, the presence of a target endonuclease in a sample can be measured by an increase in T2 when the restriction site is cleaved, resulting in the dispersion of the aggregates.

EXAMPLES

The invention is further described in the following examples, which do not limit the scope of the invention described in the claims.

Example 1

Synthesis of Superparamagnetic Iron Oxide Nanoparticles

Biocompatible, fluid phase magnetic nanoparticles ($NH_2$—CLIO) were synthesized as described and reacted with N-succinimidyl 3-(2-pyridyldithio)propionate (SPDP) to yield 2Py-SS-CLIO (FIG. 1). See Josephson et al, (1999) *Bioconjugate Chemistry*, 10, 186-91 and Perez et al., (2002) *Journal of the American Chemical Society*, 124, 2856-2857.

The first step in the synthesis of amino-CLIO is the synthesis of a dextran coated superparamagnetic iron oxide. A pure dextran coated superparamagnetic iron oxide is reacted with a crosslinking agent (5-50% epichlorohydrin) in strong base (final concentration 1-3 M NaOH). After 24 hours at room temperature, liquid ammonia in excess is then added to aminate the polysaccharide. Low molecular weight impurities were removed by exhaustive ultrafiltration using a membrane with a 10 kDa cutoff.

Example 2

Synthesis of Oligonucleotides and Alkanethiol-oligonucleotides

The 5'-alkanethiol-oligonucleotide (HS—$(CH_2)_6$—CGC-ATT-CAG-GAT (SEQ ID NO:1)) and 3'-alkanethiol-oligonucleotide (TCT-CAA-CTC-GTA(SEQ ID NO:2)-$(CH_2)_3$—SH) were synthesized at a 1 µmol-scale using standard phosphoramidite chemistry. The sulfhydryl groups were protected with a mercaptoalkyl linker. Immediately before reaction with 2Py-SS-CLIO, oligonucleotides were deprotected with dithiothreitol (DTT) (J. J. Storhoff, R. Elghanian, R. C. Mucic, C. A. Mirkin, R. L. Letsinger, J Am Chem Soc 1998, 120, 1959).

Complementary (5' TAC-GAG-TTG-AGA-ATC-CTG-AAT-GCG³')(SEQID NO:13), half-complementary (5' TAC-GAG-TTG-AGA-GAG-TGC-CCA-CAT³') (SEQ ID NO:14), and non-complementary (5'ATG-CTA-AAT-GAC-GAC-TGC-CCA-CAT³') (SEQ ID NO:15) oligonucleotides were synthesized using standard phosphoramidite chemistry (underlined bases will hybridize).

Example 3

Conjugation of Nano-Particles to Alkanethiol Oligonucleotide

To 1.1 mL of 2Py-SS-CLIO (3 mg of Fe in 0.1 M phosphate buffer, pH 8.0, see example 1), 550 µg of either 5'- or 3'-alkanethiooligonucleotide was added and incubated overnight at room temperature. The mixture was purified using an LS+ high gradient magnetic separation column (Miltenyi Biotec, Auburn, Calif.) equilibrated with 0.1 M phosphate buffer, pH 7.5. The number of oligonucleotides attached per particle was determined by treatment with DTT, followed by separation of iron and oligonucleotide using a microconcentrator as above. Oligonucleotide concentration was then determined from absorbance at 260 nm, using an extinction coefficient of $1.2 \times 10^5 \text{ M}^{-1}\text{cm}^{-1}$. The probes are denoted P1 (CLIO-SS—$(CH_2)_6$—CGC-ATT-CAG-GAT(SEQ ID NO:1)) and P2 (TCT-CAA-CTC-GTA (SEQ ID NO:2)-$(CH_2)_3$—SS-CLIO. To 1.1 mL of 2Py-SS-CLIO (3 mg of Fe in 0.1 M phosphate buffer, pH 8.0), 550 µg of either the 5-alkanethiol-oligonucleotide (HS—$(CH_2)_6$—CGC-ATT-CAG-GAT(SEQ ID NO:1)) or the 3-alkanethiol-oligonucleotide (TCT-CAA-CTC-GTA-(SEQ ID NO:2)$(CH_2)_3$—SH) were added and incubated overnight at room temperature. The next day the mixture was applied to a magnetic separations column (Miltenyi Biotec, Auburn, Calif.) equilibrated with 0.1 M phosphate buffer, pH 7.5. The column was washed with phosphate buffer to remove any non-bound oligonucleotide.

Example 4

Assay for Target Oligonucleotide

Hybridization: To generate FIGS. 2A to 2D, equal volumes (25 µL) of P1 and P2 (both at 550 µg Fe/mL) were mixed with 14 µL of 1 M NaCl, 0.1 M phosphate, pH 7.5. Two µL (400 ng) of various oligonucleotides were then added. The mixture was heated to 50° C. for 5 minutes and allowed to react at room temperature overnight. The precipitate shown in FIGS. 3A and 3B were obtained after overnight incubation of P1/P2 with complementary oligonucleotide; the precipitate was washed with 0.1 M NaCl, 0.1 M phosphate buffer and resuspended in 300 µL of the same buffer. The sample was split into two 15 µL portions and electrophoresed without DTT (lane 1) or with 4 mM DTT (lane 2) under non-denaturing conditions (FIG. 3A) or denaturing conditions (FIG. 3B).

Gel electrophoresis: Non-denaturing gels (10% polyacrylamide) and denaturing gels (20% polyacrylamide) were used after optimization of the separation process. Gels were stained with SYBR Gold dye (Molecular Probes, Eugene Oreg.).

Determination of Proton Relaxation Times: Relaxation time measurements were performed at 0.47 Tesla, at 40° C. (Bruker NMR Minispec, Billerica, Mass.), except for the experiment used to generate FIG. 5, where temperatures of 40° C. and 80° C. were used. To determine the effect of hybridization on water T2, equal amounts of P1 and P2 (5 µL) were diluted in 1 mL 1 M NaCl, 0.1 M phosphate buffer, pH 7.5 to give a total iron of 10 µg/mL. T2 values were obtained before and after addition of 1 µL (390 ng) of complementary, half-complementary or non-complementary target nucleic acids and plotted as a function of time. Relaxivity was determined by plotting water 1/T2 and 1/T1 as a function of iron concentration, see Table 2. The size of conjugates was determined by light scattering (Coulter N4, Hialeah, Fla.).

Example 5

Use of Nanoparticle Conjugates in Turbid Media

Equimolar amounts in iron of oligonucleotide-nanoparticle conjugates denoted P1 and P2 were diluted in a 10% Fat Emulsion (Intralipid® 10%, Baxter Healthcare Corporation) containing 1 M NaCl. Changes in water T2 relaxation time were recorded after addition of 1 µL (53 femtomoles) of complementary oligonucleotide. As was the case in non-turbid media (FIG. 4), a rapid decrease in the T2 relaxation time is observed (FIG. 4). Three hours after adding the complementary oligonucleotide, at the arrow, 2 µL of DTT (0.4 M) was added to the P1 and P2 solution. A gradual increase in the T2 relaxation time is observed reaching the original T2 value within two hours. These results indicate that the new methods work even in turbid media.

Example 6

Array Based Assay

Equimolar amounts in iron of oligonucleotide-nanoparticles denoted P1 and P2 were diluted with 1 M NaCl in 0.1 M sodium phosphate, pH 7.4 to give iron concentrations of 6 µg/mL or 3 µl/mL. 100 µL of the P1/P2 mixture and 1 µL of complementary or non-complementary target oligonucleotides were added to 24 of the square wells of a 384-well microtiter plate. Images were made on a clinical MR imager (GE Signal, 1.5 Tesla) using a T2-weighted pulse sequence (TR=3000 ms/TE=300 ms). FIG. 7 shows 24 wells of the 384-well plate. The top two rows contain 3 µg Fe/ml and the bottom two rows contain 6 µg Fe/ml. Each column has the indicated amounts of target nucleic acids added. The wells get "darker," i.e., the signal intensity drops because T2 drops. This is due to a hybridization-induced formation of aggregates between oligonucleotide-nanoparticle. No binding occurs with non-complementary targets, and thus, there is no change in T2 and no change in signal intensity. These results illustrate the utility of the new methods for use in in vitro arrays, which can be two- or three-dimensional.

Example 7

Assay for Green Fluorescent Protein (GFP) mRNA by Imaging MRS

To test whether MRS could be used to identify a target sequence in a higher throughput format, a panel of cell lines was screened for GFP mRNA expression using an MR imager as a detector. The panel consisted of primary human and rodent tumor cells lines, one of which was transduced with a GFP encoding HSV amplicon (Gli-36), while another one was transiently transfected with a GFP encoding plasmid DNA (COS-1). In addition, the corresponding parental cell lines were transfected with beta galactosidase as a negative control and included in the panel. Total RNA from these cell lines was isolated and imaged after sensing with GFP-P1/GFP-P2 (FIG. 9a). The sample in well C3 contained RNA from the Gli-36 cells line, whereas well D4 contained RNA from COS-1 cells. The observed magnetic changes correlated well with fluorescence measurements of the cell lines and RT-PCR (data not shown). Both parental and beta galactosidase expressing Gli-36 and COS-1 cell lines did not show a significant difference compared to wild type cell lines.

Figure 9C:
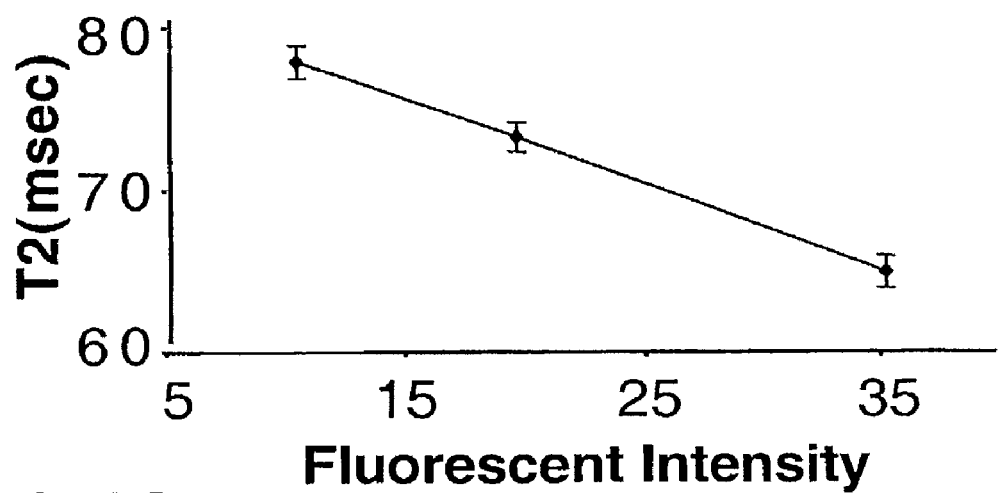
FIG. 9C is a graph illustrating GFP fluorescence and T2 relaxation time measurements of GFP mRNA indicating that the two measurements correlate well in whole cell lysate experiments indicating that mRNA is readily detectable by MR imaging.
Figure 11:
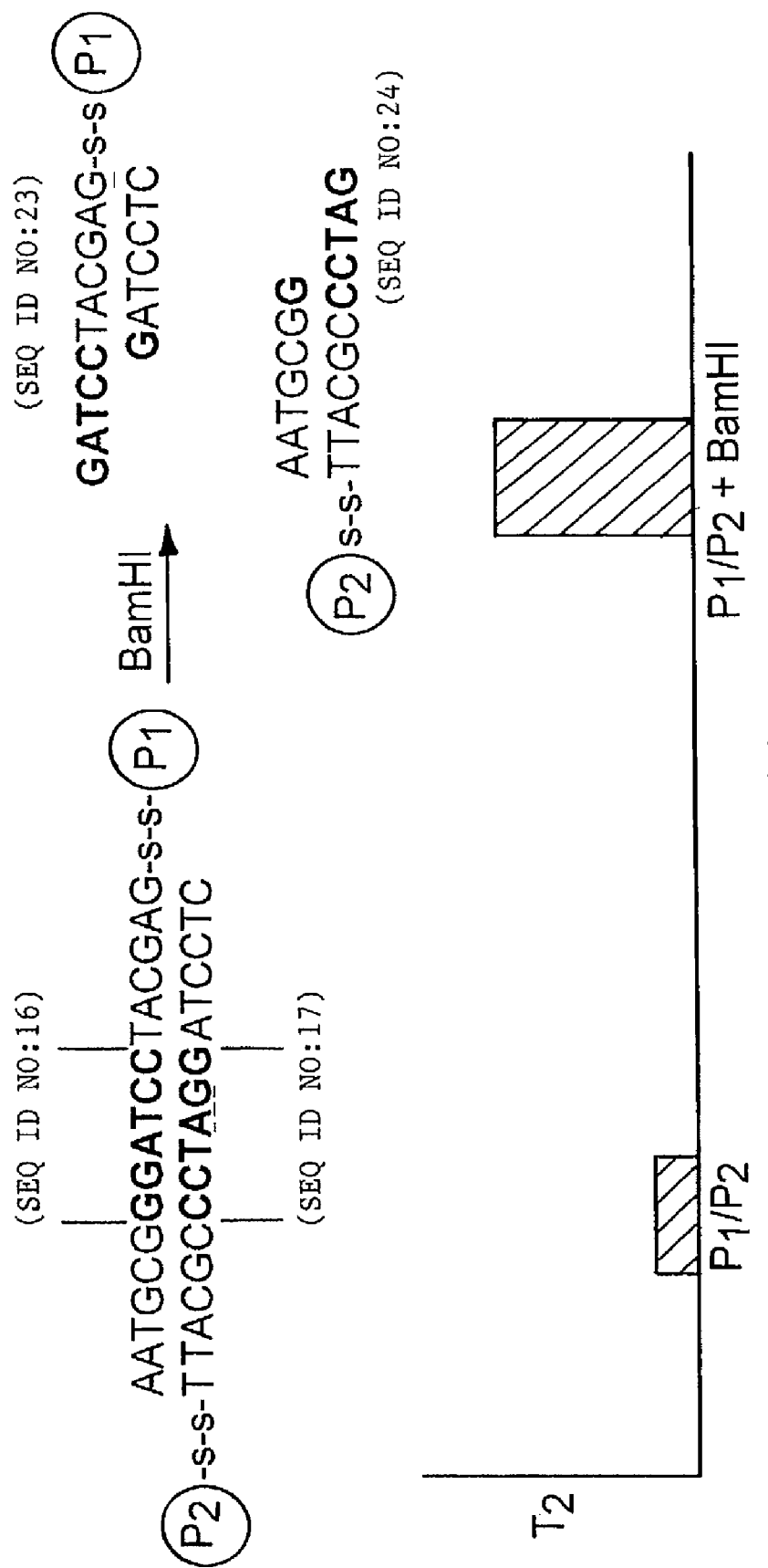
FIG. 11 is a schematic image of a small aggregate held together by double stranded oligonucleotide (P1/P2). Sequence specific cleavage by BamHI results in separation of the particles in the aggregate with a corresponding increase in T2 relaxation times.

While the above experiments were carried out with isolated RNA, similar measurements were made in cell lysates. For these experiments, a mild lysis buffer (20 mM Tris pH 8, 5 mM MgCl$_2$, 0.5% NP-40, 200 μg/mL tRNA) was added to adherent cells prior to probing with P1/P2. This buffer has been previously used to extract RNA from cell without the need of scrapping the cells off the dish. As shown in FIG. 9b, differences in GFP mRNA expression between the parental and GFP expressing Gli-36 cell lines were clearly identified. In additional studies, this difference was quantified using Gli-36 cell lines infected with different MOI of a GFP bearing amplicon vector. FIG. 9c shows the correlation between cell fluorescence measurements and mRNA measurements using MRS technology in cell lysates. In these studies, a specific GFP mRNA was detected in a pool of total RNA (1 μg) and in whole cell lysate with no prior amplification of the signal. This level of detection with the MRS technology is comparable to traditional fluorescent-based methods for oligonucleotide hybridization carried out with purified total RNA.

Example 8

Assay for Caspase Activity Using a Monobiotinylated Peptide and Avidin to Induce Formation of Small Aggregates In this assay, a biotinylated peptide substrate for caspase-3 was synthesized (Biotin-GDEVDGC (SEQ ID NO:18) caspase-3 recognition site is underlined) and coupled to aminated CLIO using SPDP (see example 1). Equimolar amounts of Avidin-CLIO and Biotinylated peptide-CLIO conjugate were incubated in PBS (10 μg Fe/ml) to allow a small aggregate to form. The T2 was measured before and after addition of 25 ng Caspase 3 (1.7 nM) in the presence or absent of a caspase 3 inhibitor. See figure after example 10b.

The avidin-CLIO construct was made as follows: Amino-CLIO (0.2 mmoles Fe) and fluorescein labeled hen egg white avidin (7.5×10$^{-5}$ mmoles) (Pierce, Rockford, Ill.) were dialyzed against 0.01M sodium acetate buffer, pH 6.0 for 2 hours. Sodium periodate (46 μmol) was added to the avidin, incubated for 30 min at room temperature in the dark, and dialyzed against 150 mM sodium chloride. The oxidized avidin was added to amino-CLIO, and the pH adjusted by the addition of 100 μl of 0.2 M sodium bicarbonate, pH 9.5. The mixture was incubated for 2.5 hours with stirring. Sodium cyanoborohydride was added (80 μmol) and the mixture was incubated for 3.5 hours at room temperature. The avidin-CLIO nanoparticle was separated from unreacted avidin using a magnetic separation column (Miltenyi Biotec, Auburn, Calif.). Iron was determined spectrophotometrically, and protein by the BCA method (Pierce). The number of avidins attached per nanoparticle was calculated using a molecular weight of 67 kDa for avidin and 2064 Fe atoms per crystal for CLIO.

FIG. 10b shows that in the absence of caspase or in the presence of caspase inhibitor, the binding moiety is intact and therefore, so is the aggregate. When the inhibitor is not added or capase is added, the aggregate is dispersed resulting in an increase of T2. These experiments indicate that the assay system has the sensitivity to detect enzyme activity in solution.

Example 9

Assay for Protein (GFP) Using a Biotinylated Polyclonal Anti-GFP

Avidin-CLIO nanoparticles made as described above were reacted with biotinylated polyclonal anti-GFP (Research Diagnostics Inc.) and were then attached to the particles. Unreacted molecules were removed. To probe for protein-protein interactions, GFP (33 μmol, 200 nM) was incubated with anti-GFP-CLIO (10 μg Fe/ml) and T2 relaxation times were recorded (FIG. 10a).

The results show that the presence of the antibodies resulted in a decrease of T2, indicating that the antibody conjugates were bound to the antigen target resulting in aggregate formation.

Example 10

Assay for Caspase Using a Dibiotinylated Peptide

In this assay, a dibiotinylated peptide is synthesized that includes between the two biotins a "substrate" (cleavage site) that can be cleaved by the protease caspase. An example of a biotinylated peptide that is convenient to make has the general structure biotin-G-X1-X2-X3-X4-G-K-biotin, wherein X1 to X4 are residues providing protease specificity (the cleavage site was between X1 and X4). FmocK(Dde) can be used in the synthesis of the peptide. It can be deprotected with 2% hydrazine and biotin coupled to the epsilon amino group of lysine. Alternatively, a biotinylated form of lysine can be purchased. Biotin is added to the N terminus of the peptide through the carboxyl group of biotin using HOBT/HBTU as activating/coupling agents.

To perform the assay, the dibiotinylated peptide is incubated with the protease and cleavage allowed to occur. Avidin-CLIO, made as described herein, is then added. When mixed with dibiotinylated peptide, small aggregates form (if no protease is present). If the dibiotinylated peptide was cleaved, by a protease such as caspase, the monobiotinylated products bind to the avidin-CLIO, but do not induce the formation of small aggregates.

Example 11

Assay for Endonuclease Using Aggregates of Double-Stranded Oligonucleotides

Two self-complementary 3'-alkanethiololigonucleotides: AAT-GCG-GGATCC-TAC-GAG-(CH$_2$)$_3$—SH (SEQ ID NO:16) and CTC-CTA-GGATC-CGC-ATT-(CH$_2$)$_3$—SH (SEQ ID NO:17) were conjugated to nanoparticles as described in Example 3. The resulting conjugates (Magnetic Relaxation Switches, MRS), denoted P1 (AAT-GCG-GGATCC-TAC-GAG-(CH$_2$)$_3$—S—S-CLIO) and P2 (CTC-CTA-GGATC-CGC-ATT-(CH$_2$)$_3$—S—S-CLIO) have on average 3 oligonucleotides per particle. The formation of MRS aggregates upon mixing P1 and P2 was determined by atomic force microscopy (AFM) (Dimension 3100, Digital Instruments). Images were recorded using tapping mode and a surface area of 5×5 μm.

The restriction endonuclease digestion was performed at 37° C. with 0.4 U/μl of BamHI, (New England BioLabs) in 500 μl of 10 mM Tris HCl, 10 mM MgCl$_2$, 50 mM NaCl pH 7.4 containing the MRS aggregate P1/P2 (10 μg of Fe/mL). The water relaxation of the solution was measured at either time intervals or after a one-hour incubation and compared to control samples (with no enzyme) using a 0.47 T NMR relaxometer (Bruker NMR Minispec, Billerica, Mass.).

Figure 12B:
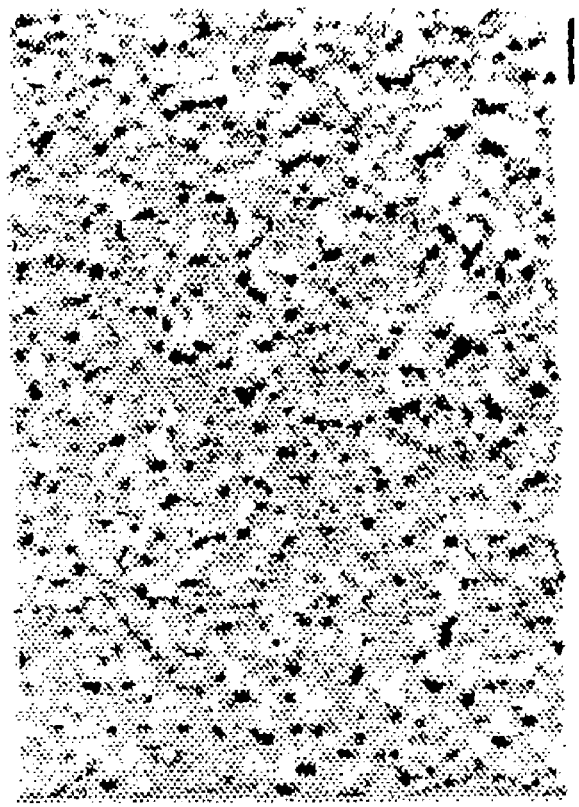
FIGS. 12A and 12B are atomic force micrographs, of the conjugates of FIG. 11 before (aggregates of FIG. 12A) and after (dispersed conjugates of FIG. 12B) addition of BamHI treatment.
Figure 12A:
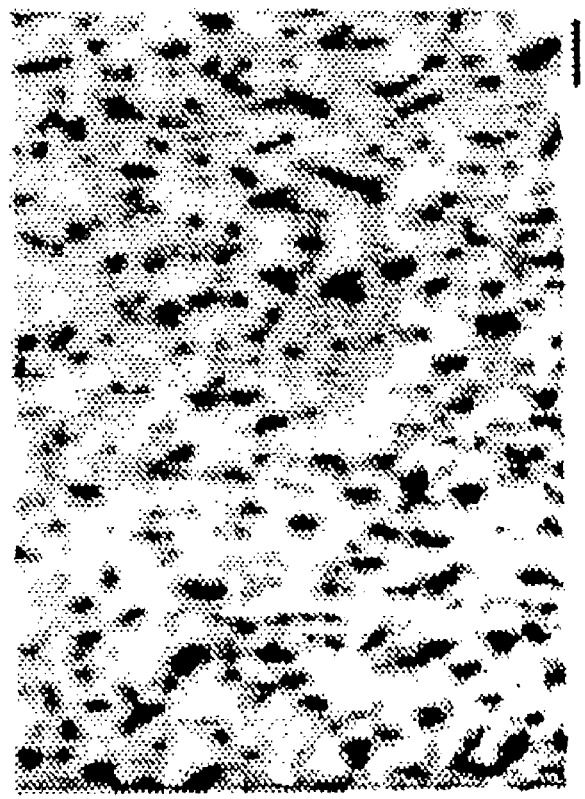

The oligonucleotide sequences were chosen so that P1 and P2 would self-hybridize with the formation of a MRS aggregate that exhibits a more pronounce effect on T2. A pair of MRS(P1 and P2) that self-assemble to form a BamHI recognition site (FIG. 1a) was prepared. P1 (10 μg Fe/mL) had a T2 of 61.6±0.3 msec, while P2 (10 μg Fe/mL) had a T2 of 60.4±0.5 msec. Meanwhile, the T2 of an equimolar mixture of P1 and P2 (total 10 μg Fe/mL) had a T2 of 32.3±0.6 msec (p<0.0001), due to self-hybridization of the particles and formation of aggregates. Incubation with BamHI, resulted in an increase in T2 back to baseline levels (59.4±0.4 msec). T2 changes were specifically inhibited by the addition of a synthetic complementary oligonucleotide and other endonucleases did not cause an increase in T2. Atomic force microscopy revealed that P1/P2 consisted of stable aggregates with average sizes raging from 300 to 400 nm (FIG. 12a). After a one-hour incubation with BamHI, the aggregates were no longer present and monodisperse nanoparticle conjugates (50-60 nm) were observed instead (FIG. 12b).

Example 12

Protein Assay Using Monoclonal Antibody-Nanoparticle Conjugates

Monoclonal antibodies can be coupled to polymer coated magnetic nanoparticles using a variety of chemistries (see, e.g., Weissleder et al., U.S. Pat. No. 5,492,814; and Kang et al. (2002) Bioconjugate Chemistry, 13, 122-127). A useful method is that of Kang because it uses the amino-CLIO chemistry described above and avoids destroying the dextran with oxidative treatments with periodate.

In this assay format a P1 (first monoclonal attached to a nanoparticle) and P2 (second monoclonal attached to a nanoparticle) are synthesized in separate reactions. The target protein must contain epitopes for both monoclonals, so that small aggregates can form in solution. If a target antigen is in solution, the monoclonal antibodies will bind both epitopes on the antigen, thereby aggregating the nanoparticles, resulting in a decrease of T2.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the presence of a target molecule in a sample, the method comprising
obtaining a mixture of at least two different populations of conjugates that specifically bind to the target molecule to form an aggregate, wherein each conjugate in the first population comprises a nanoparticle comprising a magnetic metal oxide linked to a plurality of first binding moieties that bind to a first binding site on the target molecule, and wherein each conjugate in the second population comprises a nanoparticle comprising a magnetic metal oxide linked to a plurality of second binding moieties that bind to a second binding site on the target molecule different than the first binding site;
contacting the mixture with a fluid sample under conditions that enable the first and second binding moieties to specifically bind to any target molecules in the sample and form an aggregate of conjugates; and
determining the presence of one or more aggregates in the sample by measuring the spin-spin (T2) relaxation time of the fluid sample, wherein the one or more aggregates remain in solution for at least the duration of the T2 measurement, wherein an increase in the number of aggregates within the fluid sample reduces the measured T2 relaxation time, and wherein a decrease in the T2 relaxation time of the fluid indicates the presence of the target molecule in the sample.

2. The method of claim 1, wherein the target molecule is a nucleic acid, the first binding moieties are first oligonucleotides that are complementary to a first region of the target nucleic acid, and the second binding moieties are second oligonucleotides that are complementary to a second region of the target nucleic acid.

3. The method of claim 1, wherein the target molecule is a polypeptide, the first binding moieties are first antibodies that specifically bind to a first binding site of the target polypeptide, and the second binding moieties are second antibodies that specifically bind to a second binding site of the target polypeptide.

4. The method of claim 3, wherein the first and second antibodies are monoclonal antibodies.

5. The method of claim 1, wherein the fluid is optically transparent.

6. The method of claim 1, wherein the fluid is optically translucent.

7. The method of claim 1, wherein the fluid is optically turbid.

8. The method of claim 1, wherein the fluid is optically opaque.

9. The method of claim 1, wherein the fluid is water, saline, buffered saline, or a biological fluid.

10. The method of claim 9, wherein the biological fluid is blood, a cell homogenate, a tissue homogenate, a cell extract, a tissue extract, a cell suspension, a tissue suspension, milk, urine, saliva, semen, or spinal fluid.

11. The method of claim 1, wherein the magnetic metal oxide is a superparamagnetic metal oxide.

12. The method of claim 11, wherein the superparamagnetic metal oxide comprises iron oxide.

13. The method of claim 1, wherein the metal oxides are monodisperse.

14. The method of claim 1, wherein the metal oxides are polydisperse.

15. The method of claim 1, wherein the aggregate has a size from about 100 nm to about 500 nm.

16. An assay system for determining the presence of a target molecule in a sample, the system comprising:
(i) a mixture of at least two different populations of conjugates that specifically bind to the target molecule to form an aggregate, wherein each conjugate in the first population comprises a nanoparticle comprising a magnetic metal oxide linked to a plurality of first binding moieties that bind to a first binding site on the target molecule, and wherein each conjugate in the second population comprises a nanoparticle comprising a magnetic metal oxide linked to a plurality of second binding moieties that bind to a second binding site on the target molecule different than the first binding site,
(ii) a sample container for containing the mixture when combined with a fluid sample under conditions that enable the first and second binding moieties to specifically bind to any target molecules in the sample and form an aggregate of conjugates, wherein an increase in the number of aggregates within the fluid sample reduces the measured T2 relaxation time, wherein the aggregates remain in solution for at least the duration of the T2 measurement, and wherein a decrease in the T2 relaxation time of the fluid indicates the presence of the target molecule in the sample; and
(iii) a device configured to measure the T2 relaxation time of the fluid within the sample container.

17. The assay system of claim 16, wherein the sample container is a vial or one or more wells in a microtiter plate.

* * * * *

SEQUENCE LISTING

<160> NUMBER OF SEQ ID NOS: 24

<210> SEQ ID NO 1
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 1
cgcattcagg at                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 2
tctcaactcg ta                                                          12

<210> SEQ ID NO 3
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 3
tacgagttga gaatcctgaa tgcg                                             24

<210> SEQ ID NO 4
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 4
acgagttgag agatcctgaa tgcg                                             24

```
<210> SEQ ID NO 5
<211> LENGTH: 30
<212> TYPE: DNA
<213> ORGANISM: Artificial Sequence
<220> FEATURE:
<223> OTHER INFORMATION: Synthetically generated oligonucleotide

<400> SEQUENCE: 5
tacgagttga gagagtgcat cctgaatgcg                                         30

<210> SEQ ID NO 6
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 6
tacgaggttg agaatcctga atgcg                                              25

<210> SEQ ID NO 7
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 7
tacgaggttg agaatcctgg aatgcg                                             26

<210> SEQ ID NO 8
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 8
tacgagttga gactcctgaa tgcg                                               24

<210> SEQ ID NO 9
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 9
gacgagttga gaatcctgaa tgcg                                               24

<210> SEQ ID NO 10
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 10
tacgagttga gaatcctgca tgcg                                               24

<210> SEQ ID NO 11
<211> LENGTH: 24
<212> TYPE: DNA
<213> ORGANISM: Artificial Sequence
<220> FEATURE:
<223> OTHER INFORMATION: Synthetically generated oligonucleotide
```

```
<400> SEQUENCE: 11
tacgagttga gactcctcaa tgcg                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 12
tacgacttga gaatcctgca tgcg                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 13
tacgagttga gaatcctgaa tgcg                                              24

<210> SEQ ID NO 14
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 14
tacgagttga gagagtgccc acat                                              24

<210> SEQ ID NO 15
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 15
atgctaaatg acgactgccc acat                                              24

<210> SEQ ID NO 16
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 16
aatgcgggat cctacgag                                                     18

<210> SEQ ID NO 17
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 17
ctcctaggat cccgcatt                                                     18

<210> SEQ ID NO 18
```

```
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 18

Gly Asp Glu Val Asp Gly Cys
 1               5

<210> SEQ ID NO 19
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 19
taaacggcca caagttcggc gtgt                                            24

<210> SEQ ID NO 20
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 20
taaacggcca caagttcagc gtgt                                            24

<210> SEQ ID NO 21
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 21
taaacggcca caagttctgc gtgt                                            24

<210> SEQ ID NO 22
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 22
taaacggcca caagttccgc gtgt                                            24

<210> SEQ ID NO 23
<211> LENGTH: 11
<212> TYPE: DNA
<213> ORGANISM: Artificial Sequence
<220> FEATURE:
<223> OTHER INFORMATION: Synthetically generated oligonucleotide

<400> SEQUENCE: 23
gatcctacga g                                                          11

<210> SEQ ID NO 24
<211> LENGTH: 11
<212> TYPE: DNA
<213> ORGANISM: Artificial Sequence
<220> FEATURE:
<223> OTHER INFORMATION: Synthetically generated oligonucleotide
```

-continued

```
<400> SEQUENCE: 24
gatcccgcat t                                                          11
```